US011213517B2

(12) United States Patent
Kessler et al.

(10) Patent No.: US 11,213,517 B2
(45) Date of Patent: Jan. 4, 2022

(54) PHARMACEUTICAL COMBINATION COMPRISING A T-TYPE CALCIUM CHANNEL BLOCKER

(71) Applicant: IDORSIA PHARMACEUTICALS LTD, Allschwil (CH)

(72) Inventors: Melanie Kessler, Allschwil (CH); Catherine Roch, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 0 days.

(21) Appl. No.: 16/470,109

(22) PCT Filed: Dec. 15, 2017

(86) PCT No.: PCT/EP2017/082981
§ 371 (c)(1),
(2) Date: Jun. 14, 2019

(87) PCT Pub. No.: WO2018/109152
PCT Pub. Date: Jun. 21, 2018

(65) Prior Publication Data
US 2020/0016139 A1    Jan. 16, 2020

(30) Foreign Application Priority Data

Dec. 16, 2016  (WO) ................. PCT/EP2016/081455

(51) Int. Cl.
| | | |
|---|---|---|
| A61K 31/4439 | (2006.01) | |
| A61P 25/08 | (2006.01) | |
| A61K 31/20 | (2006.01) | |
| A61K 31/4015 | (2006.01) | |

(52) U.S. Cl.
CPC .......... *A61K 31/4439* (2013.01); *A61K 31/20* (2013.01); *A61K 31/4015* (2013.01); *A61P 25/08* (2018.01)

(58) Field of Classification Search
CPC ............ A61K 31/4439; A61K 31/4015; A61K 31/20; A61K 2300/00; A61P 25/08
See application file for complete search history.

(56) References Cited

U.S. PATENT DOCUMENTS

| | | |
|---|---|---|
| 1,025,872 A | 5/1912 | Hoerlein |
| 2,409,754 A | 10/1946 | Henze |
| 2,554,816 A | 5/1951 | Clapp et al. |
| 2,884,444 A | 4/1959 | Berger et al. |
| 2,948,718 A | 8/1960 | Schindler |
| 3,121,076 A | 2/1964 | Keller et al. |
| 3,459,738 A | 8/1969 | Morren |
| 3,642,775 A | 2/1972 | Schindler |
| 3,910,959 A | 10/1975 | Vallet |
| 3,984,398 A | 10/1976 | Rossi |
| 4,024,175 A | 5/1977 | Satzinger et al. |
| 4,789,680 A | 12/1988 | Meier |
| 4,943,639 A | 4/1990 | Gobert et al. |
| 5,384,330 A | 1/1995 | Dieter et al. |
| 7,935,699 B2 | 5/2011 | Berthel et al. |
| 9,932,314 B2 | 4/2018 | Siegrist et al. |
| 10,065,929 B2 | 9/2018 | Siegrist et al. |
| 10,246,426 B2 | 4/2019 | Bezencon et al. |
| 2008/0146625 A1 | 6/2008 | Berthel et al. |
| 2009/0030403 A1 | 1/2009 | Leyde |
| 2009/0325987 A1 | 12/2009 | Muthuppalniappan et al. |
| 2010/0310493 A1 | 12/2010 | Bhuniya et al. |
| 2012/0289698 A1 | 11/2012 | Ashcraft et al. |
| 2015/0329533 A1 | 11/2015 | Nam et al. |
| 2016/0106102 A1 | 4/2016 | Kuebbeler et al. |
| 2019/0375702 A1 | 12/2019 | McLaren et al. |

FOREIGN PATENT DOCUMENTS

| | | |
|---|---|---|
| EP | 0 021 121 A1 | 1/1981 |
| EP | 0 427 197 A1 | 5/1991 |
| EP | 0 835 859 A1 | 4/1998 |
| EP | 2 402 327 A1 | 1/2012 |
| EP | 2 530 078 A1 | 12/2012 |
| GB | 1 597 796 | 9/1981 |
| WO | WO 96/00218 | 1/1996 |
| WO | WO 98/28269 | 7/1998 |
| WO | WO 02/00651 | 1/2002 |
| WO | WO 02/053101 | 7/2002 |
| WO | WO 02/053160 | 7/2002 |
| WO | WO 03/037274 | 5/2003 |
| WO | WO 03/051315 | 6/2003 |
| WO | WO 03/051833 | 6/2003 |
| WO | WO 03/101423 | 12/2003 |
| WO | WO 2004/089303 | 10/2004 |

(Continued)

OTHER PUBLICATIONS

Andersen, K.E. et al., "The Synthesis of Novel GABA Uptake Inhibitors. 1. Elucidation of the Structure-Activity Studies Leading to the Choice of (R)-1-[4,4-Bis(3-methyl-2-thienyl)-3-butenyl]-3-piperidinecarboxylic Acid (Tiagabine) as an Anticonvulsant Drug Candidate," *J. Med. Chem.*, 1993, vol. 36: 1716-1725.

Anderson, M.P. et al., "Thalamic $Ca_v3.1$ T-type $Ca^{2+}$ channel plays a crucial role in stabilizing sleep," *PNAS*, 2005, vol. 102(5): 1743-1748.

Barrow, T.S. et al., "Pyridyl amides as potent inhibitors of T-type calcium channels," *Bioorganic & Medicinal Chemistry Letters*, 2011, vol. 21: 1692-1696.

Becker, A.J. et al., "Transcriptional Upregulation of $Ca_v3.2$ Mediates Epileptogenesis in the Pilocarpine Model of Epilepsy," *The Journal of Neuroscience*, 2008, vol. 28(49): 13341-13353.

Benoff, S. et al., "The effect of calcium ion channel blockers on sperm fertilization potential," *Fertility and Sterility*, 1994, vol. 62(3): 606-617.

(Continued)

*Primary Examiner* — Barbara P Badio
(74) *Attorney, Agent, or Firm* — Hoxie & Associates LLC

(57) ABSTRACT

The present invention relates to a pharmaceutical combination comprising a first active ingredient which is N-[1-(5-Cyano-pyridin-2-ylmethyl)-1H-pyrazol-3-yl]-2-[4-(1-trifluoromethyl-cyclopropyl)-phenyl]-acetamide or a pharmaceutically acceptable salt thereof and a second active ingredient which has an anti-epileptic effect, or a pharmaceutically acceptable salt thereof.

8 Claims, No Drawings

(56) References Cited

FOREIGN PATENT DOCUMENTS

| | | |
|---|---|---|
| WO | WO 2004/089306 | 10/2004 |
| WO | WO 2004/099154 | 11/2004 |
| WO | WO 2005/056532 | 6/2005 |
| WO | WO 2006/018725 | 2/2006 |
| WO | WO 2006/066968 | 6/2006 |
| WO | WO 2006/114274 | 11/2006 |
| WO | WO 2006/114313 | 11/2006 |
| WO | WO 2007/012793 | 2/2007 |
| WO | WO 2007/073497 | 6/2007 |
| WO | WO 2007/120729 | 10/2007 |
| WO | WO 2008/012227 | 1/2008 |
| WO | WO 2008/085888 | 7/2008 |
| WO | WO 2008/156726 | 12/2008 |
| WO | WO 2009/054982 | 4/2009 |
| WO | WO 2009/054983 | 4/2009 |
| WO | WO 2009/054984 | 4/2009 |
| WO | WO 2009/118596 | 10/2009 |
| WO | WO 2009/121623 | 10/2009 |
| WO | WO 2010/073011 | 7/2010 |
| WO | WO 2010/075376 | 7/2010 |
| WO | WO 2010/122089 | 10/2010 |
| WO | WO 2010/139731 | 12/2010 |
| WO | WO 2011/022315 | 2/2011 |
| WO | WO 2011/053542 | 5/2011 |
| WO | WO 2011/084402 | 7/2011 |
| WO | WO 2012/027322 | 3/2012 |
| WO | WO 2012/077932 | 6/2012 |
| WO | WO 2012/098075 | 7/2012 |
| WO | WO 2012/120397 | 9/2012 |
| WO | WO 2013/011033 | 1/2013 |
| WO | WO 2013/032351 | 3/2013 |
| WO | WO 2013/134142 | 9/2013 |
| WO | WO 2014/179564 | 11/2014 |
| WO | WO 2014/187928 | 11/2014 |
| WO | WO 2015/186056 | 12/2015 |
| WO | WO 2016/041892 | 3/2016 |
| WO | WO 2016/123533 | 8/2016 |
| WO | WO 2018/141961 | 8/2018 |
| WO | WO 2019/008034 | 1/2019 |

OTHER PUBLICATIONS

Berg, A.T. et al., "Revised terminology and concepts for organization of seizures and epilepsies: Report of the ILAE Commission on Classification and Terminology, 2005-2009," *Epilepsia*, 2010, vol. 51(4): 676-685.
Berg, A.T. et al. "New concepts in classification of the epilepsies: Entering the 21st century," *Epilepsia*, 2011, vol. 52(6): 1058-1062.
Bezençon, O. et al., "Discovery and evaluation of Cav3.2-selective T-type calcium channel blockers," *Bioorganic & Medicinal Chemistry Letters*, 2017, 6 pages.
Bezençon, O. et al., "Discovery of a Potent, Selective T-type Calcium Channel Blocker as a Drug Candidate for the Treatment of Generalized Epilepsies," *Journal of Medicinal Chemistry*, 2017, vol. 60: 9769-9789.
Bhave, G. et al., "Posttranslational Mechanisms of Peripheral Sensitization," *J Neurobiol*, 2004, vol. 61: 88-106.
Bourinet, E. et al., "Silencing of the $Ca_v3.2$ T-type calcium channel gene in sensory neurons demonstrates its major role in nociception," *The EMBO Journal*, 2005, vol. 24: 315-324.
Brodie, M.J., "Pharmacological Treatment of Drug-Resistant Epilepsy in Adults: a Practical Guide," *Curr Neurol Neurosci Rep*, 2016, vol. 16: 82, 9 pages.
Brodie, M.J. et al., "Antiepileptic drug therapy: Does mechanism of action matter?" *Epilepsy & Behavior*, 2011, vol. 21: 331-341.
Brodie, M.J. et al., "Combining antiepileptic drugs—Rational polytherapy?" *Seizure*, 2011, vol. 20: 369-375.
Broicher, T. et al., "Correlation of T-channel coding gene expression, $I_T$, and the low threshold $Ca^{2+}$ spike in the thalamus of a rat model of absence epilepsy," *Molecular and Cellular Neuroscience*, 2008, vol. 39: 384-399.

Catterall, W.A. et al., "International Union of Pharmacology. XLVIII. Nomenclature and Structure-Function Relationships of Voltage-Gated Calcium Channels," *Pharmacological Reviews*, 2005, vol. 57(4): 411-425.
Cavelier, P. et al., "Participation of low-threshold $Ca^{2+}$ spike in the Purkinje cells complex spike," *NeuroReport*, 2008, vol. 19(3): 299-303.
Cheong, E. et al., "T-type $Ca^{2+}$ channels in absence epilepsy," *Pflugers Arch—Eur J Physiol*, 2014, vol. 466: 719-734.
Cho, Y. et al., "The SAR analysis of TRPV1 agonists with the α-methylated B-region," *Bioorganic & Medicinal Chemistry Letters*, 2012, vol. 22: 5227-5231.
Choi, D. et al., "Synthesis and Anticonvulsant Activities of N-Benzyl-2-acetamidopropionamide Derivatives," *Journal of Medicinal Chemistry*, 1996, vol. 39: 1907-1916.
Coderre, T.J. et al., "Contribution of central neuroplasticity to pathological pain: review of clinical and experimental evidence," *Pain*, 1993, vol. 52: 259-285.
Destexhe, A. et al., "A Model of Spindle Rhythmicity in the Isolated Thalamic Reticular Nucleus," *Journal of Neurophysiology*, 1994, vol. 72(2): 803-818.
Eckle, V.S. et al., "Mechanisms by which a CACNA1H mutation in epilepsy patients increases seizure susceptibility," *The Journal of Physiology*, 2014, vol. 592(4): 795-809.
Ernst, W.L. et al., "Genetic Enhancement of Thalamocortical Network Activity by Elevating α1G-Mediated Low-Voltage-Activated Calcium Current Induces Pure Absence Epilepsy," *The Journal of Neuroscience*, 2009, vol. 29(6): 1615-1625.
Flatters, S.J.L., "T-type calcium channels: a potential target for the treatment of chronic pain," *Drugs of the Future*, 2005, vol. 30(6): 573-580.
Franco, V. et al., "Challenges in the clinical development of new antiepileptic drugs," *Pharmacological Research*, 2016, vol. 103: 95-104.
Giordanetto, F. et al., "T-type calcium channels inhibitors: a patent review," *Expert Opin. Ther. Patents*, 2011, vol. 21(1): 85-101.
Goldenberg, M.M., "Overview of Drugs Used For Epilepsy and Seizures," *Pharmacy and Therapeutics*, 2010, vol. 35(7): 392-415.
Graef, J.D., "An Acquired Channelopathy Involving Thalamic T-Type $Ca^{2+}$ Channels after Status Epilepticus," *The Journal of Neuroscience*, 2009, vol. 29(14): 4430-4441.
Greene, T.W. et al., "Protective Groups in Organic Synthesis," $3^{rd}$ Edition, Wiley-Interscience, 1999, 3 pages.
Gutnick, M.J. et al., "Low threshold calcium spikes, intrinsic neuronal oscillation and rhythm generation in the CNS," *Journal Neuroscience Methods*, 1989, vol. 28: 93-99.
Hall, A. et al., "Non-acidic pyrazole $EP_1$ receptor antagonists with in vivo analgesic efficacy," *Bioorganic & Medicinal Chemistry Letters*, 2008, vol. 18: 3392-3399.
Hall, K.E. et al., "Voltage-dependent calcium currents are enhances in dorsal root ganglion neurones from the Bio Bred/Worchester diabetic rat," *Journal of Physiology*, 1995, vol. 483(2): 313-322.
Heron, S.E. et al., "Extended Spectrum of Idiopathic Generalized Epilepsies Associated with CACNA1H Functional Variants," *Ann Neurol*, 2007, vol. 62: 560-568.
Hibi, S. et al., "Discovery of 2-(2-Oxo-1-phenyl-5-pyridin-2-yl-1,2-dihydropyridin-3-yl)benzonitrile (Perampanel): A Novel, Noncompetitive α-Amino-3-hydroxy-5-methyl-4-isoxazolepropanoic Acid (AMPA) Receptor Antagonist," *Journal of Medicinal Chemistry*, 2012, vol. 55: 10584-10600.
Hoekstra, M.S. et al., "Chemical Development of CI-1008, an Enantiomerically Pure Anticonvulsant," *Organic Process Research & Development*, 1997, vol. 1(1): 26-38.
Huguenard, J.R. et al., "Intrathalamic Rhythmicity Studied in vitro: Nominal T-Current Modulation Causes Robust Antioscillatory Effects," *The Journal of Neuroscience*, 1994, vol. 14(9): 5485-5502.
Iftinca, M.C., "Neuronal T-type calcium channels: What's new?" *Journal of Medicine and Life*, 2011, vol. 4(2): 126-138.
Iftinca, M.C. et al., "Regulation of neuronal T-type calcium channels," *Trends in Pharmacological Sciences*, 2009, vol. 30(1): 32-40.
International Search Report for International Application No. PCT/IB2015/054164, prepared by the International Searching Authority, dated Mar. 8, 2015, 3 pages.

(56) References Cited

OTHER PUBLICATIONS

Isabel, E. et al., "The discovery of MK-0674, an orally bioavailable cathepsin K inhibitor," *Bioorganic & Medicinal Chemistry Letters*, 2010, vol. 20: 887-892.
Jagodic, M.M., "Upregulation of the T-Type Calcium Current in Small Rat Sensory Neurons After Chronic Constrictive Injury of the Sciatic Nerve," *J Neurophysiol*, 2008, vol. 99: 3151-3156.
Jagodic, M.M., "Cell-Specific Alterations of T-Type Calcium Current in Painful Diabetic Neuropathy Enhance Excitability of Sensory Neurons," *The Journal of Neuroscience*, 2007, vol. 27(12): 3305-3316.
Jeanmonod, D. et al., "Low-threshold calcium spike bursts in the human thalamus. Common physiopathology for sensory, motor and limbic positive symptoms," *Brain*, 1996, vol. 119: 363-375.
Jevtovic-Todorovic, V. et al., "The role of peripheral T-type calcium channels in pain transmission," *Cell Calcium*, 2006, vol. 40: 197-203.
Kenda, B.M. et al., "Discovery of 4-Substituted Pyrrolidone Butanamides as New Agents with Significant Antiepileptic Activity," *Journal of Medicinal Chemistry*, 2004, vol. 47(3): 530-549.
Khosravani, H. et al., "Voltage-Gated Calcium Channels and Idiopathic Generalized Epilepsies," *Physiol Rev*, 2006, vol. 86: 941-966.
Kim, D. et al., "Lack of the Burst Firing of Thalamocortical Relay Neurons and Resistance to Absence Seizures in Mice Lacking $\alpha_{1G}$ T-Type $Ca^{2+}$ Channels," *Neuron*, 2001, vol. 31: 35-45.
Kiss, L.E. et al., "Discovery of a Long-Acting, Peripherally Selective Inhibitor of Catechol-O-methyltransferase," *Journal of Medicinal Chemistry*, 2010, vol. 53: 3396-3411.
Kwan, P. et al., "Definition of drug resistant epilepsy: Consensus proposal by the ad hoc Task Force of the ILAE Commission on Therapeutic Strategies," *Epilepsia*, 2010, vol. 51(6): 1069-1077.
Lambert, R.C. et al., "The many faces of T-type calcium channels," *Pflugers Arch—Eur J Physiol*, 2014, vol. 466: 415-423.
Latham, J.R. et al., "Selective T-Type Calcium Channel Blockade Alleviates Hyperalgesia in ob/ob Mice," *Diabetes*, 2009, vol. 58: 2656-2665.
Lee, J. et al., "Synthesis and anti-proliferative activity evaluation of N3-acyl-N5-aryl-3,5-diaminoindazole analogues as anti-head and neck cancer agent," *DARU Journal of Pharmaceutical Sciences*, 2014, vol. 22(4), 9 pages.
Lee, J. et al., "Lack of delta waves and sleep disturbances during non-rapid eye movement sleep in mice lacking $\alpha_{1G}$-subunit of T-type calcium channels," *PNAS*, 2004, vol. 101(52): 18195-18199.
Lee, J.H. et al., "Cloning and Expression of a Novel Member of the Low Voltage-Activated T-Type Calcium Channel Family," *The Journal of Neuroscience*, 1999, vol. 19(6): 1912-1921.
Llinás, R. et al., "Oscillatory Properties of Guinea-Pig Inferior Olivary Neurones and Their Pharmacological Modulation: an In Vitro Study," *J. Physiol.*, 1986, vol. 376: 163-182.
Lory, P. et al., "Calcium channelopathies in inherited neurological disorders: Relevance to drug screening for acquired channel disorders," *IDrugs*, 2010, vol. 13(7): 467-471.
Maryanoff, B.E. et al., "Anticonvulsant O-Alkyl Sulfamates. 2,3:4,5-Bis-O-(1-methylethylidene)-β-D-fructopyranose Sulfamate and Related Compounds," *Journal of Medicinal Chemistry*, 1987, vol. 30(5): 880-887.
McGivern, J.G., "Targeting N-type and T-type calcium channels for the treatment of pain," *Drug Discovery Today*, 2006, vol. 11(5/6): 245-253.
Messinger, R.B. et al., "In vivo silencing of the $Ca_v3.2$ T-type calcium channels in sensory neurons alleviates hyperalgesia in rats with streptozocin-induced diabetic neuropathy," *Pain*, 2009, 12 pages.
Miwa, H. et al., "T-Type Calcium Channel as a New Therapeutic Target for Tremor," *Cerebellum*, 2011, vol. 10: 563-569.
Nelson, M.T. et al., "The Role of T-Type Calcium Channels in Epilepsy and Pain," *Current Pharmaceutical Design*, 2006, vol. 12: 2189-2197.

Pagé, A. et al., "Novel benzimidazole derivatives as selective CB2 agonists," *Bioorganic & Medicinal Chemistry Letters*, 2008, vol. 18:3695-3700.
Park, Y.G. et al., "$Ca_v3.1$ is a tremor rhythm pacemaker in the inferior olive," *PNAS*, 2010, vol. 107(23): 10731-10736.
Perez-Reyes, E., "Molecular Physiology of Low-Voltage-Activated T-type Calcium Channels," *Physiol Rev*, 2003, vol. 83: 117-161.
Perucca, E. et al., "The pharmacological treatment of epilepsy in adults," *Lancet Neurol*, 2011, vol. 10: 446-456.
Poolos, N.P. et al., "Comparative efficacy of combination drug therapy in refractory epilepsy," *Neurology*, 2012, vol. 78: 62-68.
Powell, K.L. et al., "A $Ca_v3.2$ T-Type Calcium Channel Point Mutation Has Splice-Variant-Specific Effects on Function and Segregates with Seizure Expression in a Polygenic Rat Model of Absence Epilepsy," *The Journal of Neuroscience*, 2009, vol. 29(2): 371-380.
Remington, The Science and Practice of Pharmacy, $21^{st}$ Edition, 2005, Part 5, Pharmaceutical Manufacturing, 5 pages.
Sircar, S.S.G., "The Influence of Groups and Associated Rings on the Stability of Certain Heterocyclic Systems. Part II. The Substituted Succinimides," *J. Chem. Soc.*, 1927, 1252-1256.
Song, I. et al., "Role of the α1G T-Type Calcium Channel in Spontaneous Absence Seizures in Mutant Mice," *The Journal of Neuroscience*, 2004, vol. 24(22): 5249-5257.
Stahl, P.H. et al., "Handbook of Pharmaceutical Salts. Properties, Selection and Use" *International Union of Pure and Applied Chemistry* (IUPAC), 2008, pp. 330-350.
Stephen, L.J. et al., "Antiepileptic drug combinations—Have newer agents altered clinical outcomes?" *Epilepsy Research*, 2012, vol. 98: 194-198.
Steriade, M., "Sleep, epilepsy and thalamic reticular inhibitory neurons," *TRENDS in Neurosciences*, 2005, vol. 28(6): 317-324.
Su, H. et al., "Upregulation of a T-Type $Ca^{2+}$ Channel Causes a Long-Lasting Modification of Neuronal Firing Mode after Status Epilepticus," *The Journal of Neuroscience*, 2002, vol. 22(9): 3645-3655.
Talley, E.M. et al., "Differential Distribution of Three Members of a Gene Family Encoding Low Voltage-Activated (T-Type) Calcium Channels," *The Journal of Neuroscience*, 1999, vol. 19(6): 1895-1911.
Talley, E.M. et al., "Low-voltage-activated calcium channel subunit expression in a genetic model of absence epilepsy in the rat," *Molecular Brain Research*, 2000, vol. 75: 159-165.
Todorovic, S.M. et al., "T-type voltage-gated calcium channels as targets for the development of novel pain therapies," *British Journal of Pharmacology*, 2011, vol. 163: 484-495.
Todorovic, S.M. et al., "Regulation of T-Type Calcium Channels in the Peripheral Pain Pathway," *Channels*, 2007, vol. 1(4): 238-245.
Tsakiridou, E. et al., "Selective Increase in T-Type Calcium Conductance of Reticular Thalamic Neurons in a Rat Model of Absence Epilepsy," *The Journal of Neuroscience*, 1995, vol. 15(4): 3110-3117.
Uno, H. et al., "Studies on 3-Substituted 1,2-Benzisoxazole Derivatives. 6. Syntheses of 3-(Sulfamoylmethyl)-1,2-benzisoxazole Derivatives and Their Anticonvulsant Activities," *Journal of Medicinal Chemistry*, 1979, vol. 22(2): 180-183.
Uslaner, J.M. et al., "T-Type Calcium Channel Antagonism Decreases Motivation for Nicotine and Blocks Nicotine- and Cue-Induced Reinstatement for a Response Previously Reinforced with Nicotine," *Biol Psychiatry*, 2010, vol. 68:712-718.
Wang, X. et al., "Pd(II)-Catalyzed Hydroxyl-Directed C-H Activation/C-O Cyclization: Expedient Construction of Dihydrobenzofurans," *J. Am. Chem. Soc.*, 2010, vol. 132: 12203-12205.
Wen, X.J. et al., "Intrathecal administration of $Ca_v3.2$ and $Ca_v3.3$ antisense oligonucleotide reverses tactile allodynia and thermal hyperalgesia in rats following chronic compression of dorsal root of ganglion," *Acta Pharmacologica Sinica*, 2006, vol. 27(12): 1547-1552.
Wildburger, N.C. et al., "Neuroprotective effects of blockers for T-type calcium channels," *Molecular Neurodegeneration*, 2009, vol. 4(44), 8 pages.

(56) References Cited

OTHER PUBLICATIONS

Woods, M., "SexRx: Calcium Channel Blockers and Your Sex Life," Accessed online Apr. 11, 2017, (http://www.winhosp.org/health-library/article?id=22043), 3 pages.
Wouters, J. et al., Pharmaceutical Salts and Co-crystals, *RSC Drug Discovery*, Chapters 7-14, 10 pages.
Xie, X. et al., "Validation of High Throughput Screening Assays Against Three Subtypes of $Ca_v3$ T-Type Channels Using Molecular and Pharmacologic Approaches," *ASSAY and Drug Development Technologies*, 2007, vol. 5(2): 191-203.
Yaari, Y. et al., "Recruitment of apical dendritic T-type $Ca^{2+}$ channels by backpropagating spikes underlies de novo intrinsic bursting in hippocampal epileptogenesis," *J Physiol*, 2007, vol. 580(2): 435-450.
Yang, Y.C. et al., "The T-type calcium channel as a new therapeutic target for Parkinson's disease," *Pflugers Arch—Eur J Physiol*, 2014, vol. 466: 747-755.
Yang, Z.Q. et al., "Short-Acting T-Type Calcium Channel Antagonists Significantly Modify Sleep Architecture in Rodents," *ACS Medicinal Chemistry Letters*, 2010, vol. 1, pp. 504-509.
Zamponi, G.W. et al., "Role of voltage-gated calcium channels in epilepsy," *Pflugers Arch—Eur J Physiol*, 2010, vol. 460: 395-403.
Bezençon, Olivier, "Milestones to the Discovery of T-type Calcium Channel Blockers for the Treatment of Generalized Epilepsies," *CHIMIA*, 71(10):722-729 (2017).
Brodie, Martin J., "Antiepileptic drug therapy the story so far," *Seizure*, 19:650-655 (2010).
Kaneko, Journal of Pediatric Practice, 2015, 78(2): 199-206; Japanese translation only.
Kaneko, Journal of Pediatric Practice, 2015, 78(2): 199-206; English translation.
Brodie, MJ. "Pharmacological Treatment of Drug-Resistant Epilepsy in Adults: a Practical Guide," *Curr Neurol Neurosci Rep.*, Sep. 2016;16(9):82.
Luszczki, JJ, et al., "Interactions between oxcarbazepine and conventional antiepileptic drugs in the maximal electroshock test in mice: an isobolographic analysis," *Epilepsia*, Apr. 2003;44(4):489-99.
Luszczki, JJ, et al., "Pharmacological and behavioral characteristics of interactions between vigabatrin and conventional antiepileptic drugs in pentylenetetrazole-induced seizures in mice: an isobolographic analysis," *Neuropsychopharmacology*, May 2005;30(5):958-73.
Luszczki, JJ, et al., "Characterization of the anticonvulsant, behavioral and pharmacokinetic interaction profiles of stiripentol in combination with clonazepam, ethosuximide, phenobarbital, and valproate using isobolographic analysis," *Epilepsia*, Nov. 2006;47(11):1841-54.
Lukawski, et al., "Captopril potentiates the anticonvulsant activity of carbamazepine and lamotrigine in the mouse maximal electroshock seizure model," *J. Neural Transm.*, 2010; 117:1161-1166.

PHARMACEUTICAL COMBINATION COMPRISING A T-TYPE CALCIUM CHANNEL BLOCKER

CROSS REFERENCE TO RELATED APPLICATIONS

This application is a United States Application under 35 U.S.C. 371 claiming benefit of PCT Application No. PCT/EP2017/082981, filed on Dec. 15, 2017, which claims the benefit of PCT Application No. PCT/EP2016/081455, filed on Dec. 16, 2016, the contents of each of which are incorporated herein by reference.

The present invention relates to a pharmaceutical combination comprising a first active ingredient which is N-[1-(5-Cyano-pyridin-2-ylmethyl)-1H-pyrazol-3-yl]-2-[4-(1-trifluoromethyl-cyclopropyl)-phenyl]-acetamide or a pharmaceutically acceptable salt thereof and a second active ingredient which has an anti-epileptic effect or a pharmaceutically acceptable salt thereof.

Epilepsy is a brain disorder characterized by an enduring predisposition to generate seizures and by the neurobiological, cognitive, psychological, and social consequences of this condition (Berg A T et al. (2011) New concepts in classification of the epilepsies: entering the 21st century. Epilepsia 52:1058-1062; Berg A T et al. (2010) Revised terminology and concepts for organization of seizures and epilepsies: report of the ILAE Commission on Classification and Terminology, 2005-2009. Epilepsia 51:676-685). Epileptic patients experience recurrent spontaneous seizures, which may present various phenotypes ranging from mild brief lapses of attention or muscle jerks up to severe and prolonged convulsions. Seizures are transient events due to abnormal, excessive, or synchronous neuronal activity in the brain. They are classified either as focal seizures when they remain restricted to networks in one hemisphere or as generalized (absence, myoclonic, tonic clonic, tonic and atonic) seizures when they rapidly engage bilaterally distributed networks.

Anti-epileptic drugs (AEDs) aim at reducing seizure activity. Currently approved AEDs act mainly on multiple ion channels ($Ca^{2+}$, $Na^+$, $K^+$ or $Cl^-$), synaptic systems and amino-acid receptors, on neurons and glial cells. AEDs are currently prescribed based primarily on consideration of individual's seizure type(s), comorbidities and co-medications (Perucca E et al. (2011) The pharmacological treatment of epilepsy in adults. Lancet Neurol 10:446-456; Franco V et al. (2016) Challenges in the clinical development of new antiepileptic drugs. Pharmacol Res 103:95-104) but age, sex, childbearing potential are also considered. Even today there are no reliable tools to predict clinical responses in the individual patient.

Newly diagnosed patients are given one of the first line treatment (such as Carbamazepine, Ethosuximide, Lamotrigine, Levetiracetam, Oxcarbazepine, Phenytoin, Topiramate, Valproic acid or salts thereof) chosen based on individual patient characteristics. Treatment usually starts with low dose which is up-titrated during a period which varies for each drug. Maintenance dose is typically adapted for each patient and should be the lowest dose that provides seizure freedom. This initial selected maintenance dose can be increased when seizures recur (Perucca E et al. (2011) The pharmacological treatment of epilepsy in adults. Lancet Neurol 10:446-456). Approximately 50% of adult epileptic patients will stay on monotherapy with the initial AED prescribed, meaning that they achieved seizure freedom without intolerable side effects. For the remaining 50%, treatment needs adaptation and a common option is to combine AEDs. Pharmacoresistant epilepsies represent about 30% of the epileptic population and have been defined by the International League Against Epilepsy (ILAE) as the failure to achieve seizure freedom despite adequate trials of at least two appropriately chosen and tolerated AED schedules, given alone or in combination (Kwan P et al. (2010) Definition of drug resistant epilepsy: consensus proposal by the ad hoc Task Force of the ILAE Commission on Therapeutic Strategies. Epilepsia 51:1069-1077). Most patients with refractory epilepsy take 2, 3 or 4 different AEDs. Since more than 25 AEDs are currently available in the market, there are, in theory, a huge number of possible combinations. This explains the recommendation for a rational polytherapy, i.e. combination of AEDs having different pharmacological properties (Brodie M J et al. (2011) Antiepileptic drug therapy: does mechanism of action matter? Epilepsy Behav 21:331-341; Brodie M J et al. (2011) Combining antiepileptic drugs—rational polytherapy? Seizure 20:369-375; Brodie M J (2016) Pharmacological Treatment of Drug-Resistant Epilepsy in Adults: a Practical Guide. Curr Neurol Neurosci Rep 16:82). Indeed, most successful combination therapy is observed with drugs having different mechanisms of action (Stephen L J et al. (2012) Antiepileptic drug combinations—have newer agents altered clinical outcomes? Epilepsy Res 98:194-198; Brodie M J (2016) Pharmacological Treatment of Drug-Resistant Epilepsy in Adults: a Practical Guide. Curr Neurol Neurosci Rep 16:82). However, retrospective analysis of an extensive database of AED therapy in refractory patients showed that combination of more than 2 drugs is in most cases not significantly beneficial to patients (Poolos N P et al. (2012) Comparative efficacy of combination drug therapy in refractory epilepsy. Neurology 78:62-68).

Calcium ($Ca^{2+}$) is an important signal transduction element in neurons and its entry into the cell is tightly regulated by two major classes of voltage gated calcium channels: the high-voltage activated (HVA; L-, N-, P/Q- and R-types) and the low-voltage activated (LVA; T-type) calcium channels (Catterall W A et al. (2005) International Union of Pharmacology. XLVIII. Nomenclature and structure-function relationships of voltage-gated calcium channels. Pharmacol Rev 57:411-425).

Three T-type calcium channel subtypes with different electrophysiological properties have been described: $Ca_v3.1$, $Ca_v3.2$ and $Ca_v3.3$ (Lee J H et al. (1999) Cloning and expression of a novel member of the low voltage-activated T-type calcium channel family. J Neurosci 19:1912-1921; Perez-Reyes E (2003) Molecular physiology of low-voltage-activated t-type calcium channels. Physiol Rev 83:117-161). T-type calcium channels are widely expressed in the brain (Talley E M et al. (1999) Differential distribution of three members of a gene family encoding low voltage-activated (T-type) calcium channels. J Neurosci 19:1895-1911), where they play an important role in the control of rhythmic neuronal burst firing and resultant thalamocortical oscillations (Cheong E et al. (2014) T-type Ca(2+) channels in absence epilepsy. Pflugers Arch 466:719-734; Lambert R C et al. (2014) The many faces of T-type calcium channels. Pflugers Arch 466:415-423).

Abnormal T-type calcium channel mediated oscillations can be observed during idiopathic generalized epilepsies (IGE) seizures, in particular absence seizures, in both humans and animals (Khosravani H et al. (2006) Voltage-gated calcium channels and idiopathic generalized epilepsies. Physiol Rev 86:941-966; Zamponi G W et al. (2010) Role of voltage-gated calcium channels in epilepsy. Pflugers Arch 460:395-403; Cheong E et al. (2014) T-type Ca(2+) channels in absence epilepsy. Pflugers Arch 466:719-734).

In line with these observations, mutations were identified in the gene expressing the $Ca_v3.2$ subtype in patients with childhood absence epilepsy and other forms of IGE (Khosravani H et al. (2006) Voltage-gated calcium channels and idiopathic generalized epilepsies. Physiol Rev 86:941-966; Heron S E et al. (2007) Extended spectrum of idiopathic generalized epilepsies associated with CACNA1H functional variants. Ann Neurol 62:560-568; Zamponi G W et al. (2010) Role of voltage-gated calcium channels in epilepsy. Pflugers Arch 460:395-403; Eckle V S et al. (2014) Mechanisms by which a CACNA1H mutation in epilepsy patients increases seizure susceptibility. J Physiol 592:795-809). Several of these mutations increase the intrinsic activity of the channels, whereas others increase the intracellular trafficking of the channels to the plasma membrane; most mutations enhance calcium currents. A direct consequence of this is increased excitability in neurons that exhibit enhanced bursting activity, thereby contributing to the generation of epileptiform discharges. Several rodent models confirm the importance of the $Ca_v3.2$ channel subtype. In genetic rat models of spontaneous absence-like epilepsy (GAERS, Genetic Absence Epilepsy in Rats from Strasbourg; WAG/Rij), a gain-of-function mutation of the $Ca_v3.2$ gene has been reported (Powell K L et al. (2009) A $Ca_v3.2$ T-type calcium channel point mutation has splice-variant-specific effects on function and segregates with seizure expression in a polygenic rat model of absence epilepsy. J Neurosci 29:371-380), as well as elevated levels of $Ca_v3.2$ mRNA, and increased T-type calcium currents (Tsakiridou E et al. (1995) Selective increase in T-type calcium conductance of reticular thalamic neurons in a rat model of absence epilepsy. J Neurosci 15:3110-3117; Talley E M et al. (2000) Low-voltage-activated calcium channel subunit expression in a genetic model of absence epilepsy in the rat. Brain Res Mol Brain Res 75:159-165; Broicher T et al. (2008) Correlation of T-channel coding gene expression, IT, and the low threshold Ca2+ spike in the thalamus of a rat model of absence epilepsy. Mol Cell Neurosci 39:384-399; Powell K L et al. (2009) A $Ca_v3.2$ T-type calcium channel point mutation has splice-variant-specific effects on function and segregates with seizure expression in a polygenic rat model of absence epilepsy. J Neurosci 29:371-380). Acquired channelopathies involving long-term alterations in thalamic $Ca_v3.2$ channels have also been described for a mouse model of temporal lobe epilepsy (Graef J D et al. (2009) An acquired channelopathy involving thalamic T-type Ca2+ channels after status epilepticus. J Neurosci 29:4430-4441).

Several lines of evidence link mutations in the $Ca_v3.1$ subtype with epilepsy in humans and in rodent animal models. Genetic variants have been detected in patients with juvenile myoclonic epilepsy, another form of IGE (Lory P et al. (2010) Calcium channelopathies in inherited neurological disorders: Relevance to drug screening for acquired channel disorders. IDrugs 13:467-471). Overexpression of $Ca_v3.1$ channels in mice leads to frequent bilateral cortical seizures (Ernst W L et al. (2009) Genetic enhancement of thalamo-cortical network activity by elevating alpha 1g-mediated low-voltage-activated calcium current induces pure absence epilepsy. J Neurosci 29:1615-1625) and $Ca_v3.1$ knockout mice are protected from absence seizures (Kim D et al. (2001) Lack of the burst firing of thalamocortical relay neurons and resistance to absence seizures in mice lacking alpha (1G) T-type Ca(2+) channels. Neuron 31:35-45; Song I et al. (2004) Role of the alpha1G T-type calcium channel in spontaneous absence seizures in mutant mice. J Neurosci 24:5249-5257).

It was surprisingly found that N-[1-(5-Cyano-pyridin-2-ylmethyl)-1H-pyrazol-3-yl]-2-[4-(1-trifluoromethyl-cyclopropyl)-phenyl]-acetamide showed a synergistic effect in a mouse model of generalized tonic-clonic seizures when administered together with existing AEDs.

DESCRIPTION OF THE INVENTION

1) In a first embodiment the present invention relates to a pharmaceutical combination comprising a first active ingredient which is N-[1-(5-Cyano-pyridin-2-ylmethyl)-1H-pyrazol-3-yl]-2-[4-(1-trifluoromethyl-cyclopropyl)-phenyl]-acetamide (hereinafter also referred to as "COMPOUND 1") or a pharmaceutically acceptable salt thereof and a second active ingredient which has an anti-epileptic effect, or a pharmaceutically acceptable salt thereof.

COMPOUND 1 is a selective and orally available triple T-type calcium channel blocker, i.e. COMPOUND 1 blocks the three T-type calcium channel subtypes $Ca_v3.1$, $Ca_v3.2$ and $Ca_v3.3$. COMPOUND 1 has been described to be useful in the prevention/prophylaxis and/or treatment of diseases or disorders where calcium T channels are involved and especially in the treatment of epilepsy (WO 2015/186056). COMPOUND 1 may be prepared according to the procedure as disclosed in WO 2015/186056.

It is to be understood that the present invention encompasses COMPOUND 1 in any form including amorphous as well as crystalline forms of COMPOUND 1. It is further to be understood that crystalline forms of COMPOUND 1 encompasses all types of crystalline forms of COMPOUND 1 including polymorphs of the mere molecule, solvates and hydrates, molecular salts and co-crystals (when the same molecule can be co-crystallized with different co-crystal formers) provided they are suitable for pharmaceutical administration.

2) A further embodiment of the invention relates to a pharmaceutical combination according to embodiment 1), wherein the second active ingredient is selected from the group consisting of 5H-dibenzo[b,f]azepine-5-carboxamide (Carbamazepine), (RS)-3-ethyl-3-methyl-pyrrolidine-2,5-dione (Ethosuximide), 6-(2,3-dichlorophenyl)-1,2,4-triazine-3,5-diamine (Lamotrigine), (S)-2-(2-oxopyrrolidin-1-yl) butanamide (Levetiracetam), 10,11-dihydro-10-oxo-5H-dibenz[b,f]azepine-5-carboxamide (Oxcarbazepine), 2-propylpentanoic acid (Valproic acid), N-(5-sulfamoyl-1,3,4-thiadiazol-2-yl)acetamide (Acetazolamide), (2S)-2-[(4R)-2-oxo-4-propylpyrrolidin-1-yl]butanamide (Brivaracetam), 7-chloro-1-methyl-5-phenyl-1,5-benzodiazepine-2,4-dione (Clobazam), 5-(2-chlorophenyl)-7-nitro-1,3-dihydro-1,4-benzodiazepin-2-one (Clonazepam), (S)-10-acetoxy-10,11-dihydro-5H-dibenz[b,f]azepine-5-carboxamide (Eslicarbazepine acetate), (3-carbamoyloxy-2-phenylpropyl) carbamate (Felbamate), 1-(aminomethyl)cyclohexaneacetic acid (Gabapentin), (R)-2-acetamido-N-benzyl-3-methoxy-propanamide (Lacosamide), 5'-(2-cyanophenyl)-1'-phenyl-2,3'-bipyridinyl-6'(1'H)-one (Perampanel), 5-ethyl-5-phenyl-1,3-diazinane-2,4,6-trione (Phenobarbital), 5,5-diphenylimidazolidine-2,4-dione (Phenytoin), 2-(2-oxopyrrolidin-1-yl)acetamide (Piracetam), (3S)-3-(aminomethyl)-5-methylhexanoic acid (Pregabalin), 5-ethyl-5-phenyl-1,3-diazinane-4,6-dione (Primidone), ethyl (2-amino-4-((4-fluorobenzyl)amino)phenyl)carbamate (Retigabine), 1-(2,6-difluorobenzyl)-1H-1,2,3-triazole-4-carboxamide (Rufinamide), (RS)-(E)-4,4-dimethyl-1-[3,4

(methylenedioxy)-phenyl]-1-penten-3-ol (Stiripentol), (3R)-1-[4,4-bis(3-methyl-2-thienyl)-3-buten-1-yl]-3-piperidinecarboxylic acid (Tiagabine), 2,3:4,5-bis-O-(1-methylethylidene)-β-D-fructopyranose sulfamate (Topiramate), (RS)-4-aminohex-5-enoic acid (Vigabatrin), and benzo[d]isoxazol-3-ylmethanesulfonamide (Zonisamide); or a pharmaceutically acceptable salt of any of the aforementioned.

Carbamazepine (5H-dibenzo[b,f]azepine-5-carboxamide) is described to be effective for the treatment of focal seizures and tonic clonic seizures. Pharmaceutical compositions comprising Carbamazepine are available in different dosage forms such as tablets, chewtabs, suspensions and suppositories; tablets are also available in a prolonged release form. The average total dose administered per day for adults is 600 to 2000 mg and is typically given in 2 to 4 doses. Carbamazepine can be prepared according to procedures known in the art, for example as described in U.S. Pat. No. 2,948,718.

(RS)-3-ethyl-3-methyl-pyrrolidine-2,5-dione (Ethosuximide) is described to be effective for the treatment of absence seizures. Pharmaceutical compositions comprising Ethosuximide are available in different dosage forms such as capsules or syrups. The average total dose administered per day for adults is 750 to 1500 mg and is typically given in 2 or 3 doses. Ethosuximide can be prepared according to procedures known in the art, for example as described in Sircar S S G (1927), J. Chem. Soc. 1252-1256.

6-(2,3-dichlorophenyl)-1,2,4-triazine-3,5-diamine (Lamotrigine) is described to be effective for the treatment of focal seizures and tonic clonic seizures. Pharmaceutical compositions comprising Lamotrigine are available in different dosage forms such as tablets and dispersible tablets. The average total dose administered per day for adults is 100 to 400 mg and is typically given in 1 or 2 doses. Lamotrigine can be prepared according to procedures known in the art, for example as described in EP 0021121.

(S)-2-(2-oxopyrrolidin-1-yl)butanamide (Levetiracetam) is described to be effective for the treatment of focal seizures, tonic clonic seizures and myoclonic seizures. Pharmaceutical compositions comprising Levetiracetam are available in different dosage forms such as tablets and oral solutions. The average total dose administered per day for adults is 1000 to 3000 mg and is typically given in 2 doses. Levetiracetam can be prepared according to procedures known in the art, for example as described in U.S. Pat. No. 4,943,639.

10,11-dihydro-10-oxo-5H-dibenz[b,f]azepine-5-carboxamide (Oxcarbazepine) is described to be effective for the treatment of focal seizures and secondarily generalized seizures. Pharmaceutical compositions comprising Oxcarbazepine are available in different dosage forms such as tablets and oral suspensions. The average total dose administered per day for adults is 1200 to 2400 mg and is typically given in 2 or 3 doses. Oxcarbazepine can be prepared according to procedures known in the art, for example as described in U.S. Pat. No. 3,642,775.

2-propylpentanoic acid (Valproic acid) is described to be effective for the treatment of focal seizures, tonic clonic seizures and absence seizures. It is understood that sodium valproate is a preferred pharmaceutically acceptable salt of valproic acid. It is further understood that any reference to "valproic acid or a pharmaceutically acceptable salt thereof" refers to valproic acid, to a pharmaceutically acceptable salt of valproic acid (especially sodium valproate) and to a mixture of valproic acid and a pharmaceutically acceptable salt of valproic acid such as especially a mixture of valproic acid and sodium valproate (notably a mixture in a 1:1 molar ratio: divalproex sodium, Valproate semisodium). Pharmaceutical compositions comprising valproic acid and/or sodium valproate are available in different dosage forms such as tablets, crushable tablets, liquids and syrups; tablets and granules are also available in a prolonged release form. The average total dose administered per day for adults is 400 to 2000 mg and is typically given in 1 or 2 doses. Valproic acid and sodium valproate can be prepared according to procedures known in the art, for example as described in EP 0835859.

N-(5-sulfamoyl-1,3,4-thiadiazol-2-yl)acetamide (Acetazolamide) is described to be effective for the treatment of focal seizures, tonic clonic seizures and absence seizures. Pharmaceutical compositions comprising Acetazolamide are available in different dosage forms such as tablets and powder; capsules are available in a prolonged release form. The average total dose administered per day for adults is 250 to 1000 mg and is typically given in 2 or 3 doses. Acetazolamide can be prepared according to procedures known in the art, for example as described in U.S. Pat. No. 2,554,816.

(2S)-2-[(4R)-2-oxo-4-propylpyrrolidin-1-yl]butanamide (Brivaracetam) is described to be effective for the treatment of focal seizures. Pharmaceutical compositions comprising Brivaracetam are available in different dosage forms such as tablets and solutions. The average total dose administered per day for adults is 50 to 200 mg and is typically given in 2 doses. Brivaracetam can be prepared according to procedures known in the art, for example as described in Kenda B M et al. (2004), J. Med. Chem., 47, 530-549.

7-chloro-1-methyl-5-phenyl-1,5-benzodiazepine-2,4-dione (Clobazam) is described to be effective for the treatment of focal seizures and tonic clonic seizures. Pharmaceutical compositions comprising Clobazam are available in different dosage forms such as tablets and suspensions. The average total dose administered per day for adults is 20 to 60 mg and is typically given in 1 or 2 doses. Clobazam can be prepared according to procedures known in the art, for example as described in U.S. Pat. No. 3,984,398.

5-(2-chlorophenyl)-7-nitro-1,3-dihydro-1,4-benzodiazepin-2-one (Clonazepam) is described to be effective for the treatment of focal seizures, tonic clonic seizures, myoclonic seizures and absence seizures. Pharmaceutical compositions comprising Clonazepam are available in different dosage forms such as tablets and solutions. The average total dose administered per day for adults is 1 to 4 mg and is typically given in 2 doses. Clonazepam can be prepared according to procedures known in the art, for example as described in U.S. Pat. No. 3,121,076.

(S)-10-acetoxy-10,11-dihydro-5H-dibenz[b,f]azepine-5-carboxamide (Eslicarbazepine acetate) is described to be effective for the treatment of focal seizures. Pharmaceutical compositions comprising Eslicarbazepine acetate are available as tablets. The average total dose administered per day for adults is 800 to 1200 mg and is typically given in 1 dose. Eslicarbazepine acetate can be prepared according to procedures known in the art, for example as described in WO 2007/012793.

(3-carbamoyloxy-2-phenylpropyl) carbamate (Felbamate) is described to be effective for the treatment of focal seizures and tonic clonic seizures. Pharmaceutical compositions comprising Felbamate are available in different dosage forms such as tablets and suspensions. The average total dose administered per day for adults is 1200 to 3600 mg and is typically given in 3 or 4 doses. Felbamate can be prepared according to procedures known in the art, for example as described in U.S. Pat. No. 2,884,444.

1-(aminomethyl)cyclohexaneacetic acid (Gabapentin) is described to be effective for the treatment of focal seizures. Pharmaceutical compositions comprising Gabapentin are available in different dosage forms such as tablets, capsules and solutions. The average total dose administered per day for adults is 1800 to 3600 mg and is typically given in 3 doses. Gabapentin can be prepared according to procedures known in the art, for example as described in U.S. Pat. No. 4,024,175.

(R)-2-acetamido-N-benzyl-3-methoxypropanamide (Lacosamide) is described to be effective for the treatment of focal seizures. Pharmaceutical compositions comprising Lacosamide are available in different dosage forms such as tablets, solutions and syrups. The average total dose administered per day for adults is 200 to 400 mg and is typically given in 2 doses. Lacosamide can be prepared according to procedures known in the art, for example as described in Choi D et al. (1996), J. Med. Chem., 39, 1907-1916.

5'-(2-cyanophenyl)-1'-phenyl-2,3'-bipyridinyl-6'(1'H)-one (Perampanel) is described to be effective for the treatment of focal seizures and tonic clonic seizures. Pharmaceutical compositions comprising Perampanel are available as tablets. The average total dose administered per day for adults is 4 to 12 mg and is typically given in 1 dose. Perampanel can be prepared according to procedures known in the art, for example as described in Hibi S et al. (2012), J. Med. Chem., 55(23), 10584-10600.

5-ethyl-5-phenyl-1,3-diazinane-2,4,6-trione (Phenobarbital) is described to be effective for the treatment of focal seizures and tonic clonic seizures. Pharmaceutical compositions comprising Phenobarbital are available in different dosage forms such as tablets and solutions. The average total dose administered per day for adults is 30 to 180 mg and is typically given in 2 doses. Phenobarbital can be prepared according to procedures known in the art, for example as described in U.S. Pat. No. 1,025,872.

5,5-diphenylimidazolidine-2,4-dione (Phenytoin) is described to be effective for the treatment of focal seizures and tonic clonic seizures. It is understood that Phenytoin sodium is a preferred pharmaceutically acceptable salt of Phenytoin. It is further understood that any reference to "Phenytoin or a pharmaceutically acceptable salt thereof" refers to Phenytoin and to a pharmaceutically acceptable salt of Phenytoin (especially Phenytoin sodium). Pharmaceutical compositions comprising Phenytoin or Phenytoin sodium are available in different dosage forms such as tablets, chewable tablets, capsules, solutions and suspensions. The average total dose administered per day for adults is 150 to 500 mg and is typically given in 1 or 2 doses. Phenytoin can be prepared according to procedures known in the art, for example as described in U.S. Pat. No. 2,409,754.

2-(2-oxopyrrolidin-1-yl)acetamide (Piracetam) is described to be effective for the treatment of myoclonic seizures. Pharmaceutical compositions comprising Piracetam are available in different dosage forms such as tablets and solutions. The average total dose administered per day for adults is 7.2 to 24 mg and is typically given in 2 or 3 doses. Piracetam can be prepared according to procedures known in the art, for example as described in U.S. Pat. No. 3,459,738.

(3S)-3-(aminomethyl)-5-methylhexanoic acid (Pregabalin) is described to be effective for the treatment of focal seizures. Pharmaceutical compositions comprising Pregabalin are available in different dosage forms such as capsules and solutions. The average total dose administered per day for adults is 300 to 600 mg and is typically given in 2 doses. Pregabalin can be prepared according to procedures known in the art, for example as described in Hoekstra et al., Org. Process Res. Dev. 1997, 1, 26-38.

5-ethyl-5-phenyl-1,3-diazinane-4,6-dione (Primidone) is described to be effective for the treatment of focal seizures and tonic clonic seizures. Pharmaceutical compositions comprising Primidone are available as tablets. The average total dose administered per day for adults is 500 to 1500 mg and is typically given in 2 to 4 doses. Primidone can be prepared according to procedures known in the art, for example as described in GB 1597796.

ethyl (2-amino-4-((4-fluorobenzyl)amino)phenyl)carbamate (Retigabine) is described to be effective for the treatment of focal seizures. Pharmaceutical compositions comprising Retigabine are available as tablets. The average total dose administered per day for adults is 900 to 1200 mg and is typically given in 3 doses. Retigabine can be prepared according to procedures known in the art, for example as described in U.S. Pat. No. 5,384,330 or in WO 2012/098075.

1-(2,6-difluorobenzyl)-1H-1,2,3-triazole-4-carboxamide (Rufinamide) is described to be effective for the treatment of seizures associated with Lennox-Gastaut syndrome. Pharmaceutical compositions comprising Rufinamide are available in different dosage forms such as tablets and suspensions. The average total dose administered per day for adults is 200 to 3600 mg and is typically given in 2 doses. Rufinamide can be prepared according to procedures known in the art, for example as described in U.S. Pat. No. 4,789,680.

(RS)-(E)-4,4-dimethyl-1-[3,4(methylenedioxy)-phenyl]-1-penten-3-ol (Stiripentol) is described to be effective for the treatment of tonic clonic seizures in severe myoclonic epilepsy in infancy (SMEI or Dravet syndrome). Pharmaceutical compositions comprising Stiripentol are available in different dosage forms such as capsules and powder. The average total dose administered per day for adults is up to 50 mg/kg and is typically given in 2 or 3 doses. Stiripentol can be prepared according to procedures known in the art, for example as described in DE 2308494.

(3R)-1-[4,4-bis(3-methyl-2-thienyl)-3-buten-1-yl]-3-piperidinecarboxylic acid (Tiagabine) is described to be effective for the treatment of focal seizures. It is understood that (3R)-1-[4,4-bis(3-methyl-2-thienyl)-3-buten-1-yl]-3-piperidinecarboxylic acid hydrochloride is a preferred pharmaceutically acceptable salt of Tiagabine. It is further understood that any reference to "(3R)-1-[4,4-bis(3-methyl-2-thienyl)-3-buten-1-yl]-3-piperidinecarboxylic acid or a pharmaceutically acceptable salt thereof" refers to (3R)-1-[4,4-bis(3-methyl-2-thienyl)-3-buten-1-yl]-3-piperidinecarboxylic acid and to a pharmaceutically acceptable salt of (3R)-1-[4,4-bis(3-methyl-2-thienyl)-3-buten-1-yl]-3-piperidinecarboxylic acid (especially (3R)-1-[4,4-bis(3-methyl-2-thienyl)-3-buten-1-yl]-3-piperidinecarboxylic acid hydrochloride). Pharmaceutical compositions comprising (3R)-1-[4,4-bis(3-methyl-2-thienyl)-3-buten-1-yl]-3-piperidinecarboxylic acid and/or (3R)-1-[4,4-bis(3-methyl-2-thienyl)-3-buten-1-yl]-3-piperidinecarboxylic acid hydrochloride are available as tablets. The average total dose administered per day for adults is 30 to 45 mg and is typically given in 1 to 3 doses. (3R)-1-[4,4-bis(3-methyl-2-thienyl)-3-buten-1-yl]-3-piperidinecarboxylic acid and (3R)-1-[4,4-bis(3-methyl-2-thienyl)-3-buten-1-yl]-3-piperidinecarboxylic acid hydrochloride can be prepared according to procedures known in the art, for example as described in Andersen et al., J. Med. Chem. 1993, 36(12), 1716.

2,3:4,5-bis-O-(1-methylethylidene)-β-D-fructopyranose sulfamate (Topiramate) is described to be effective for the treatment of focal seizures and tonic clonic seizures. Pharmaceutical compositions comprising Topiramate are available in different dosage forms such as tablets and capsules. The average total dose administered per day for adults is 200 to 400 mg and is typically given in 2 doses. Topiramate can be prepared according to procedures known in the art, for example as described in Maryanoff et al., J. Med. Chem. 1987, 30(5), 880.

(RS)-4-aminohex-5-enoic acid (Vigabatrin) is described to be effective for the treatment of focal seizures. Pharmaceutical compositions comprising Vigabatrin are available in different dosage forms such as tablets and granules. The average total dose administered per day for adults is 1000 to 4000 mg and is typically given in 1 or 2 doses. Vigabatrin can be prepared according to procedures known in the art, for example as described in EP 0427197.

benzo[d]isoxazol-3-ylmethanesulfonamide (Zonisamide) is described to be effective for the treatment of focal seizures. Pharmaceutical compositions comprising Zonisamide are available as capsules. The average total dose administered per day for adults is 300 to 500 mg and is typically given in 1 or 2 doses. Zonisamide can be prepared according to procedures known in the art, for example as described in Uno et al., J. Med. Chem. 1979, 22(2), 180.

3) A further embodiment of the invention relates to a pharmaceutical combination according to embodiment 1), wherein the second active ingredient is selected from the group consisting of 5H-dibenzo[b,f]azepine-5-carboxamide (Carbamazepine), (RS)-3-ethyl-3-methyl-pyrrolidine-2,5-dione (Ethosuximide), 6-(2,3-dichlorophenyl)-1,2,4-triazine-3,5-diamine (Lamotrigine), (S)-2-(2-oxopyrrolidin-1-yl)butanamide (Levetiracetam), 10,11-dihydro-10-oxo-5H-dibenz[b,f]azepine-5-carboxamide (Oxcarbazepine), 2-propylpentanoic acid (Valproic acid), 5,5-diphenylimidazolidine-2,4-dione (Phenytoin), and 2,3:4,5-bis-O-(1-methylethylidene)-β-D-fructopyranose sulfamate (Topiramate); or a pharmaceutically acceptable salt of any of the aforementioned.

4) A further embodiment of the invention relates to a pharmaceutical combination according to embodiment 1), wherein the second active ingredient is selected from the group consisting of 5H-dibenzo[b,f]azepine-5-carboxamide (Carbamazepine), (RS)-3-ethyl-3-methyl-pyrrolidine-2,5-dione (Ethosuximide), 6-(2,3-dichlorophenyl)-1,2,4-triazine-3,5-diamine (Lamotrigine), (S)-2-(2-oxopyrrolidin-1-yl)butanamide (Levetiracetam), 10,11-dihydro-10-oxo-5H-dibenz[b,f]azepine-5-carboxamide (Oxcarbazepine), and 2-propylpentanoic acid (Valproic acid); or a pharmaceutically acceptable salt of any of the aforementioned.

5) A further embodiment of the invention relates to a pharmaceutical combination according to embodiment 1), wherein the second active ingredient is selected from the group consisting of 5H-dibenzo[b,f]azepine-5-carboxamide (Carbamazepine), (RS)-3-ethyl-3-methyl-pyrrolidine-2,5-dione (Ethosuximide), 6-(2,3-dichlorophenyl)-1,2,4-triazine-3,5-diamine (Lamotrigine), 10,11-dihydro-10-oxo-5H-dibenz[b,f]azepine-5-carboxamide (Oxcarbazepine), 2-propylpentanoic acid (Valproic acid), 7-chloro-1-methyl-5-phenyl-1,5-benzodiazepine-2,4-dione (Clobazam), 5-(2-chlorophenyl)-7-nitro-1,3-dihydro-1,4-benzodiazepin-2-one (Clonazepam), 5-ethyl-5-phenyl-1,3-diazinane-2,4,6-trione (Phenobarbital), 5,5-diphenylimidazolidine-2,4-dione (Phenytoin), 5-ethyl-5-phenyl-1,3-diazinane-4,6-dione (Primidone), 2,3:4,5-bis-O-(1-methylethylidene)-β-D-fructopyranose sulfamate (Topiramate), and benzo[d]isoxazol-3-ylmethanesulfonamide (Zonisamide); or a pharmaceutically acceptable salt of any of the aforementioned.

6) A further embodiment of the invention relates to a pharmaceutical combination according to embodiment 1), wherein the second active ingredient is selected from the group consisting of (RS)-3-ethyl-3-methyl-pyrrolidine-2,5-dione (Ethosuximide), 6-(2,3-dichlorophenyl)-1,2,4-triazine-3,5-diamine (Lamotrigine), 2-propylpentanoic acid (Valproic acid), and 2,3:4,5-bis-O-(1-methylethylidene)-β-D-fructopyranose sulfamate (Topiramate); or a pharmaceutically acceptable salt of any of the aforementioned.

7) A further embodiment of the invention relates to a pharmaceutical combination according to embodiment 1), wherein the second active ingredient is selected from the group consisting of (RS)-3-ethyl-3-methyl-pyrrolidine-2,5-dione (Ethosuximide), 6-(2,3-dichlorophenyl)-1,2,4-triazine-3,5-diamine (Lamotrigine), and 2-propylpentanoic acid (Valproic acid); or a pharmaceutically acceptable salt of any of the aforementioned.

8) A further embodiment of the invention relates to a pharmaceutical combination according to embodiment 1), wherein the second active ingredient is selected from the group consisting of 5H-dibenzo[b,f]azepine-5-carboxamide (Carbamazepine), 6-(2,3-dichlorophenyl)-1,2,4-triazine-3,5-diamine (Lamotrigine), 10,11-dihydro-10-oxo-5H-dibenz[b,f]azepine-5-carboxamide (Oxcarbazepine), 2-propylpentanoic acid (Valproic acid), 7-chloro-1-methyl-5-phenyl-1,5-benzodiazepine-2,4-dione (Clobazam), 5-ethyl-5-phenyl-1,3-diazinane-2,4,6-trione (Phenobarbital), 5,5-diphenylimidazolidine-2,4-dione (Phenytoin), 5-ethyl-5-phenyl-1,3-diazinane-4,6-dione (Primidone), 2,3:4,5-bis-O-(1-methylethylidene)-β-D-fructopyranose sulfamate (Topiramate), and benzo[d]isoxazol-3-ylmethanesulfonamide (Zonisamide); or a pharmaceutically acceptable salt of any of the aforementioned.

9) A further embodiment of the invention relates to a pharmaceutical combination according to embodiment 1), wherein the second active ingredient is selected from the group consisting of 6-(2,3-dichlorophenyl)-1,2,4-triazine-3,5-diamine (Lamotrigine), 2-propylpentanoic acid (Valproic acid), and 2,3:4,5-bis-O-(1-methylethylidene)-3-D-fructopyranose sulfamate (Topiramate); or a pharmaceutically acceptable salt of any of the aforementioned.

10) A further embodiment of the invention relates to a pharmaceutical combination according to embodiment 1), wherein the second active ingredient is selected from the group consisting of (RS)-3-ethyl-3-methyl-pyrrolidine-2,5-dione (Ethosuximide), 6-(2,3-dichlorophenyl)-1,2,4-triazine-3,5-diamine (Lamotrigine), (S)-2-(2-oxopyrrolidin-1-yl)butanamide (Levetiracetam), 2-propylpentanoic acid (Valproic acid), and 5-(2-chlorophenyl)-7-nitro-1,3-dihydro-1,4-benzodiazepin-2-one (Clonazepam); or a pharmaceutically acceptable salt of any of the aforementioned.

11) A further embodiment of the invention relates to a pharmaceutical combination according to embodiment 1), wherein the second active ingredient is selected from the group consisting of (RS)-3-ethyl-3-methyl-pyrrolidine-2,5-dione (Ethosuximide), and 2-propylpentanoic acid (Valproic acid); or a pharmaceutically acceptable salt of any of the aforementioned.

12) A further embodiment of the invention relates to a pharmaceutical combination according to embodiment 1), wherein the second active ingredient is selected from the group consisting of 5H-dibenzo[b,f]azepine-5-carboxamide (Carbamazepine), (S)-2-(2-oxopyrrolidin-1-yl)butanamide (Levetiracetam), 10,11-dihydro-10-oxo-5H-dibenz[b,f]azepine-5-carboxamide (Oxcarbazepine), 2-propylpentanoic acid (Valproic acid), (2S)-2-[(4R)-2-oxo-4-propylpyrrolidin-1-yl]butanamide (Brivaracetam), 7-chloro-1- methyl-5-phenyl-1,5-benzodiazepine-2,4-dione (Clobazam), (S)-10-acetoxy-10,11-dihydro-5H-dibenz[b,f]azepine-5-carboxamide (Eslicarbazepine acetate), 1-(aminomethyl)cyclohexaneacetic acid (Gabapentin), (R)-2-acetamido-N-benzyl-3-methoxypropanamide (Lacosamide), 5'-(2-cyanophenyl)-1'-phenyl-2,3'-bipyridinyl-6'(1'H)-one (Perampanel), 5-ethyl-5-phenyl-1,3-diazinane-2,4,6-trione (Phenobarbital), 5,5-diphenylimidazolidine-2,4-dione (Phenytoin), (3S)-3-(aminomethyl)-5-methylhexanoic acid (Pregabalin), 5-ethyl-5-phenyl-1,3-diazinane-4,6-dione (Primidone), ethyl (2-amino-4-((4-fluorobenzyl)amino)phenyl) carbamate (Retigabine), 1-(2,6-difluorobenzyl)-1H-1,2,3-triazole-4-carboxamide (Rufinamide), (3R)-1-[4,4-bis(3-methyl-2-thienyl)-3-buten-1-yl]-3-piperidinecarboxylic acid (Tiagabine), 2,3:4,5-bis-O-(1-methylethylidene)-3-D-fructopyranose sulfamate (Topiramate), (RS)-4-aminohex-5-enoic acid (Vigabatrin), and benzo[d]isoxazol-3-ylmethanesulfonamide (Zonisamide); or a pharmaceutically acceptable salt of any of the aforementioned.

13) A further embodiment of the invention relates to a pharmaceutical combination according to embodiment 1), wherein the second active ingredient is selected from the group consisting of 5H-dibenzo[b,f]azepine-5-carboxamide (Carbamazepine), (S)-2-(2-oxopyrrolidin-1-yl)butanamide (Levetiracetam), 10,11-dihydro-10-oxo-5H-dibenz[b,f]azepine-5-carboxamide (Oxcarbazepine), 2-propylpentanoic acid (Valproic acid), (S)-10-acetoxy-10,11-dihydro-5H-dibenz[b,f]azepine-5-carboxamide (Eslicarbazepine acetate), 1-(aminomethyl)cyclohexaneacetic acid (Gabapentin), (R)-2-acetamido-N-benzyl-3-methoxypropanamide (Lacosamide), 5-ethyl-5-phenyl-1,3-diazinane-2,4,6-trione (Phenobarbital), 5,5-diphenylimidazolidine-2,4-dione (Phenytoin), (3S)-3-(aminomethyl)-5-methylhexanoic acid (Pregabalin), 5-ethyl-5-phenyl-1,3-diazinane-4,6-dione (Primidone), 1-(2,6-difluorobenzyl)-1H-1,2,3-triazole-4-carboxamide (Rufinamide), (3R)-1-[4,4-bis(3-methyl-2-thienyl)-3-buten-1-yl]-3-piperidinecarboxylic acid (Tiagabine), 2,3:4,5-bis-O-(1-methylethylidene)-β-D-fructopyranose sulfamate (Topiramate), and benzo[d]isoxazol-3-ylmethanesulfonamide (Zonisamide); or a pharmaceutically acceptable salt of any of the aforementioned.

14) A further embodiment of the invention relates to a pharmaceutical combination according to embodiment 1), wherein the second active ingredient is selected from the group consisting of 5H-dibenzo[b,f]azepine-5-carboxamide (Carbamazepine), (S)-2-(2-oxopyrrolidin-1-yl)butanamide (Levetiracetam), 10,11-dihydro-10-oxo-5H-dibenz[b,f]azepine-5-carboxamide (Oxcarbazepine), and 2-propylpentanoic acid (Valproic acid); or a pharmaceutically acceptable salt of any of the aforementioned.

15) A further embodiment of the invention relates to a pharmaceutical combination according to embodiment 1), wherein the second active ingredient is selected from the group consisting of 5H-dibenzo[b,f]azepine-5-carboxamide (Carbamazepine), 10,11-dihydro-10-oxo-5H-dibenz[b,f]azepine-5-carboxamide (Oxcarbazepine), 2-propylpentanoic acid (Valproic acid), and 5,5-diphenylimidazolidine-2,4-dione (Phenytoin); or a pharmaceutically acceptable salt of any of the aforementioned.

16) A further embodiment of the invention relates to a pharmaceutical combination according to embodiment 1), wherein the second active ingredient is selected from the group consisting of 6-(2,3-dichlorophenyl)-1,2,4-triazine-3,5-diamine (Lamotrigine), 2-propylpentanoic acid (Valproic acid), 5-(2-chlorophenyl)-7-nitro-1,3-dihydro-1,4-benzodiazepin-2-one (Clonazepam), 2-(2-oxopyrrolidin-1-yl)acetamide (Piracetam), and 2,3:4,5-bis-O-(1-methylethylidene)-β-D-fructopyranose sulfamate (Topiramate); or a pharmaceutically acceptable salt of any of the aforementioned.

17) A further embodiment of the invention relates to a pharmaceutical combination according to embodiment 1), wherein the second active ingredient is selected from the group consisting of (S)-2-(2-oxopyrrolidin-1-yl)butanamide (Levetiracetam), and 2-propylpentanoic acid (Valproic acid); or a pharmaceutically acceptable salt of any of the aforementioned.

18) A further embodiment of the invention relates to a pharmaceutical combination according to embodiment 1), wherein the second active ingredient is 5H-dibenzo[b,f]azepine-5-carboxamide (Carbamazepine) or a pharmaceutically acceptable salt thereof.

19) A further embodiment of the invention relates to a pharmaceutical combination according to embodiment 1), wherein the second active ingredient is (RS)-3-ethyl-3-methyl-pyrrolidine-2,5-dione (Ethosuximide) or a pharmaceutically acceptable salt thereof.

20) A further embodiment of the invention relates to a pharmaceutical combination according to embodiment 1), wherein the second active ingredient is 6-(2,3-dichlorophenyl)-1,2,4-triazine-3,5-diamine (Lamotrigine) or a pharmaceutically acceptable salt thereof.

21) A further embodiment of the invention relates to a pharmaceutical combination according to embodiment 1), wherein the second active ingredient is (S)-2-(2-oxopyrrolidin-1-yl)butanamide (Levetiracetam) or a pharmaceutically acceptable salt thereof.

22) A further embodiment of the invention relates to a pharmaceutical combination according to embodiment 1), wherein the second active ingredient is 10,11-dihydro-10-oxo-5H-dibenz[b,f]azepine-5-carboxamide (Oxcarbazepine) or a pharmaceutically acceptable salt thereof.

23) A further embodiment of the invention relates to a pharmaceutical combination according to embodiment 1), wherein the second active ingredient is 2-propylpentanoic acid (Valproic acid) or a pharmaceutically acceptable salt thereof.

24) A further embodiment of the invention relates to a pharmaceutical combination according to embodiment 1), wherein the second active ingredient is N-(5-sulfamoyl-1,3,4-thiadiazol-2-yl)acetamide (Acetazolamide) or a pharmaceutically acceptable salt thereof.

25) A further embodiment of the invention relates to a pharmaceutical combination according to embodiment 1), wherein the second active ingredient is (2S)-2-[(4R)-2-oxo-4-propylpyrrolidin-1-yl]butanamide (Brivaracetam) or a pharmaceutically acceptable salt thereof.

26) A further embodiment of the invention relates to a pharmaceutical combination according to embodiment 1), wherein the second active ingredient is 7-chloro-1-methyl-5-phenyl-1,5-benzodiazepine-2,4-dione (Clobazam) or a pharmaceutically acceptable salt thereof.

27) A further embodiment of the invention relates to a pharmaceutical combination according to embodiment 1), wherein the second active ingredient is 5-(2-chlorophenyl)-7-nitro-1,3-dihydro-1,4-benzodiazepin-2-one (Clonazepam) or a pharmaceutically acceptable salt thereof.

28) A further embodiment of the invention relates to a pharmaceutical combination according to embodiment 1), wherein the second active ingredient is (S)-10-acetoxy-10,11-dihydro-5H-dibenz[b,f]azepine-5-carboxamide (Eslicarbazepine acetate) or a pharmaceutically acceptable salt thereof.

29) A further embodiment of the invention relates to a pharmaceutical combination according to embodiment 1), wherein the second active ingredient is (3-carbamoyloxy-2-phenylpropyl) carbamate (Felbamate) or a pharmaceutically acceptable salt thereof.

30) A further embodiment of the invention relates to a pharmaceutical combination according to embodiment 1), wherein the second active ingredient is 1-(aminomethyl) cyclohexaneacetic acid (Gabapentin) or a pharmaceutically acceptable salt thereof.

31) A further embodiment of the invention relates to a pharmaceutical combination according to embodiment 1), wherein the second active ingredient is (R)-2-acetamido-N-benzyl-3-methoxypropanamide (Lacosamide) or a pharmaceutically acceptable salt thereof.

32) A further embodiment of the invention relates to a pharmaceutical combination according to embodiment 1), wherein the second active ingredient is 5'-(2-cyanophenyl)-1'-phenyl-2,3'-bipyridinyl-6'(1'H)-one (Perampanel) or a pharmaceutically acceptable salt thereof.

33) A further embodiment of the invention relates to a pharmaceutical combination according to embodiment 1), wherein the second active ingredient is 5-ethyl-5-phenyl-1,3-diazinane-2,4,6-trione (Phenobarbital) or a pharmaceutically acceptable salt thereof.

34) A further embodiment of the invention relates to a pharmaceutical combination according to embodiment 1), wherein the second active ingredient is 5,5-diphenylimidazolidine-2,4-dione (Phenytoin) or a pharmaceutically acceptable salt thereof.

35) A further embodiment of the invention relates to a pharmaceutical combination according to embodiment 1), wherein the second active ingredient is 2-(2-oxopyrrolidin-1-yl)acetamide (Piracetam) or a pharmaceutically acceptable salt thereof.

36) A further embodiment of the invention relates to a pharmaceutical combination according to embodiment 1), wherein the second active ingredient is (3S)-3-(aminomethyl)-5-methylhexanoic acid (Pregabalin) or a pharmaceutically acceptable salt thereof.

37) A further embodiment of the invention relates to a pharmaceutical combination according to embodiment 1), wherein the second active ingredient is 5-ethyl-5-phenyl-1,3-diazinane-4,6-dione (Primidone) or a pharmaceutically acceptable salt thereof.

38) A further embodiment of the invention relates to a pharmaceutical combination according to embodiment 1), wherein the second active ingredient is ethyl (2-amino-4-((4-fluorobenzyl)amino)phenyl)carbamate (Retigabine) or a pharmaceutically acceptable salt thereof.

39) A further embodiment of the invention relates to a pharmaceutical combination according to embodiment 1), wherein the second active ingredient is 1-(2,6-difluorobenzyl)-1H-1,2,3-triazole-4-carboxamide (Rufinamide) or a pharmaceutically acceptable salt thereof.

40) A further embodiment of the invention relates to a pharmaceutical combination according to embodiment 1), wherein the second active ingredient is (RS)-(E)-4,4-dimethyl-1-[3,4(methylenedioxy)-phenyl]-1-penten-3-ol (Stiripentol) or a pharmaceutically acceptable salt thereof.

41) A further embodiment of the invention relates to a pharmaceutical combination according to embodiment 1), wherein the second active ingredient is (3R)-1-[4,4-bis(3-methyl-2-thienyl)-3-buten-1-yl]-3-piperidinecarboxylic acid (Tiagabine) or a pharmaceutically acceptable salt thereof.

42) A further embodiment of the invention relates to a pharmaceutical combination according to embodiment 1), wherein the second active ingredient is 2,3:4,5-bis-O-(1-methylethylidene)-β-D-fructopyranose sulfamate (Topiramate) or a pharmaceutically acceptable salt thereof.

43) A further embodiment of the invention relates to a pharmaceutical combination according to embodiment 1), wherein the second active ingredient is (RS)-4-aminohex-5-enoic acid (Vigabatrin) or a pharmaceutically acceptable salt thereof.

44) A further embodiment of the invention relates to a pharmaceutical combination according to embodiment 1), wherein the second active ingredient is benzo[d]isoxazol-3-ylmethanesulfonamide (Zonisamide) or a pharmaceutically acceptable salt thereof.

45) A further embodiment of the invention relates to a pharmaceutical combination according to any one of embodiments 1) to 44), wherein the first and the second active ingredient are comprised in a single pharmaceutical composition.

In a special case of embodiment 45) where one active ingredient is administered more frequently than the other active ingredient, only one or several (up to the number of administrations for the less frequently administered active ingredient) of the pharmaceutical compositions needed per day will contain both, the first and the second active ingredient. For example, where one of the two active ingredients is administered once daily and the other active ingredient is administered twice daily, only one of the two pharmaceutical compositions needed per day will contain both, the first and the second active ingredient whereas the other will only contain the active ingredient that is administered twice daily.

Moreover, in case of a pharmaceutical combination according to embodiment 45) where the first and/or the second active ingredient is administered according to a dose up-titration regimen the pharmaceutical compositions needed for the dose up-titration will contain the amounts of active ingredient required for the different steps of the dose up-titration regimen.

46) A further embodiment of the invention relates to a pharmaceutical combination according to any one of embodiments 1) to 44), wherein the first and the second active ingredient are comprised in separated pharmaceutical compositions.

In case the first and the second active ingredient are comprised in separated pharmaceutical compositions, they can be administered simultaneously, sequentially or separately; preferably the separated pharmaceutical compositions are administered simultaneously or sequentially, especially sequentially. In case the first active ingredient is for example administered once daily and the second active ingredient twice daily, then the separated pharmaceutical compositions are preferably administered one time per day simultaneously or sequentially, especially sequentially. If administered sequentially or separately, the separated pharmaceutical compositions may be administered in one or the other order. The number of administrations per day may be the same or different for the separated pharmaceutical compositions. For instance, one pharmaceutical composition may be administered twice daily and the other pharmaceutical composition may be administered once or twice daily. Preferably the pharmaceutical composition comprising COMPOUND 1 is administered once daily and the pharmaceutical composition comprising the second active ingredient is administered one, two or three times per day (most preferably one or two times per day). Further, the separated pharmaceutical compositions may be administered by the same or different routes of administration, preferably by the same route of administration. Most preferably the separated pharmaceutical compositions are administered orally. The first and/or the second active ingredient may be independently from each other administered according to a dose up-titration regimen up to the respective maintenance dose; the pharmaceutical compositions comprising the first and/or the second active ingredient needed for the dose up-titration will contain the amounts of active ingredient required for the different steps of the dose up-titration regimen.

47) A further embodiment of the invention relates to a pharmaceutical combination according to any one of embodiments 1) to 46) for use as a medicament.

48) A further embodiment of the invention relates to a pharmaceutical combination according to any one of embodiments 1) to 46) for use in the prevention/prophylaxis and/or treatment of a disease or disorder associated with a dysfunction of T-type calcium channels (and notably of a disease or disorder wherein the blockade of the T-type calcium channel subtypes $Ca_v3.1$, $Ca_v3.2$ and/or $Ca_v3.3$ is indicated).

49) A further embodiment of the invention relates to a pharmaceutical combination according to any one of embodiments 1) to 46) for use in the prevention/prophylaxis and/or treatment of epilepsy (notably idiopathic generalized epilepsy).

50) A further embodiment of the invention relates to a pharmaceutical combination according to any one of embodiments 1) to 46) for use in the prevention/prophylaxis and/or treatment of focal and/or generalized seizures.

51) A further embodiment of the invention relates to a pharmaceutical combination according to any one of embodiments 1) to 46) for use in the prevention/prophylaxis and/or treatment of focal, tonic, clonic, tonic clonic, absence, myoclonic and/or atonic seizures.

52) A further embodiment of the invention relates to a pharmaceutical combination according to any one of embodiments 1) to 46) for use in the prevention/prophylaxis and/or treatment of tonic clonic, absence, myoclonic and/or atonic seizures.

53) A further embodiment of the invention relates to a pharmaceutical combination according to any one of embodiments 1) to 46) for use in the prevention/prophylaxis and/or treatment of tonic clonic and/or absence seizures.

54) A further embodiment of the invention relates to a pharmaceutical combination according to any one of embodiments 1) to 46) for use in the prevention/prophylaxis and/or treatment of tonic clonic seizures.

55) A further embodiment of the invention relates to a pharmaceutical combination according to any one of embodiments 1) to 46) for use in the prevention/prophylaxis and/or treatment of absence seizures.

The term "epilepsy" describes recurrent unprovoked seizures wherein the term "seizure" refers to an excessive and/or hypersynchronous electrical neuronal activity. Different types of "seizures" are disclosed for example in Berg et al., Epilepsia. 2010; 51(4): 676-685, which reference is herewith incorporated by reference.

The present invention also relates to a method for the prevention/prophylaxis and/or treatment of a disease or disorder listed in any one of embodiments 48) to 55) comprising administering to a subject (preferably a human subject) in need thereof a pharmaceutically active amount of a pharmaceutical combination according to any one of embodiments 1) to 46).

56) A further embodiment of the invention relates to a pharmaceutical composition containing, as active principle, N-[1-(5-Cyano-pyridin-2-ylmethyl)-1H-pyrazol-3-yl]-2-[4-(1-trifluoromethyl-cyclopropyl)-phenyl]-acetamide, or a pharmaceutically acceptable salt thereof, and at least one therapeutically inert excipient, wherein the pharmaceutical composition is to be administered in combination with a second pharmaceutical composition containing, as active principle, 5H-dibenzo[b,f]azepine-5-carboxamide (Carbamazepine), (RS)-3-ethyl-3-methyl-pyrrolidine-2,5-dione (Ethosuximide), 6-(2,3-dichlorophenyl)-1,2,4-triazine-3,5-diamine (Lamotrigine), (S)-2-(2-oxopyrrolidin-1-yl)butanamide (Levetiracetam), 10,11-dihydro-10-oxo-5H-dibenz[b,f]azepine-5-carboxamide (Oxcarbazepine), 2-propylpentanoic acid (Valproic acid), N-(5-sulfamoyl-1,3,4-thiadiazol-2-yl)acetamide (Acetazolamide), (2S)-2-[(4R)-2-oxo-4-propylpyrrolidin-1-yl]butanamide (Brivaracetam), 7-chloro-1-methyl-5-phenyl-1,5-benzodiazepine-2,4-dione (Clobazam), 5-(2-chlorophenyl)-7-nitro-1,3-dihydro-1,4-benzodiazepin-2-one (Clonazepam), (S)-10-acetoxy-10,11-dihydro-5H-dibenz[b,f]azepine-5-carboxamide (Eslicarbazepine acetate), (3-carbamoyloxy-2-phenylpropyl)carbamate (Felbamate), 1-(aminomethyl)cyclohexaneacetic acid (Gabapentin), (R)-2-acetamido-N-benzyl-3-methoxypropanamide (Lacosamide), 5'-(2-cyanophenyl)-1'-phenyl-2,3'-bipyridinyl-6'(1'H)-one (Perampanel), 5-ethyl-5-phenyl-1,3-diazinane-2,4,6-trione (Phenobarbital), 5,5-diphenylimidazolidine-2,4-dione (Phenytoin), 2-(2-oxopyrrolidin-1-yl)acetamide (Piracetam), (3S)-3-(aminomethyl)-5-methylhexanoic acid (Pregabalin), 5-ethyl-5-phenyl-1,3-diazinane-4,6-dione (Primidone), ethyl (2-amino-4-((4-fluorobenzyl)amino)phenyl)carbamate (Retigabine), 1-(2,6-difluorobenzyl)-1H-1,2,3-triazole-4-carboxamide (Rufinamide), (RS)-(E)-4,4-dimethyl-1-[3,4 (methylenedioxy)-phenyl]-1-penten-3-ol (Stiripentol), (3R)-1-[4,4-bis(3-methyl-2-thienyl)-3-buten-1-yl]-3-piperidinecarboxylic acid (Tiagabine), 2,3:4,5-bis-O-(1-methylethylidene)-β-D-fructopyranose sulfamate (Topiramate), (RS)-4-aminohex-5-enoic acid (Vigabatrin), or benzo[d]isoxazol-3-ylmethanesulfonamide (Zonisamide), or a pharmaceutically acceptable salt thereof, and at least one therapeutically inert excipient.

57) A further embodiment of the invention relates to a pharmaceutical composition containing, as active principle, N-[1-(5-Cyano-pyridin-2-ylmethyl)-1H-pyrazol-3-yl]-2-[4-(1-trifluoromethyl-cyclopropyl)-phenyl]-acetamide, or a pharmaceutically acceptable salt thereof, and at least one therapeutically inert excipient, wherein the pharmaceutical composition is to be administered in combination with a second pharmaceutical composition containing, as active principle, (RS)-3-ethyl-3-methyl-pyrrolidine-2,5-dione (Ethosuximide), 6-(2,3-dichlorophenyl)-1,2,4-triazine-3,5-diamine (Lamotrigine), (S)-2-(2-oxopyrrolidin-1-yl)butanamide (Levetiracetam), 2-propylpentanoic acid (Valproic acid), or 5-(2-chlorophenyl)-7-nitro-1,3-dihydro-1,4-benzodiazepin-2-one (Clonazepam), or a pharmaceutically acceptable salt thereof, and at least one therapeutically inert excipient.

58) A further embodiment of the invention relates to a pharmaceutical composition according to embodiment 56) or 57) for use as a medicament.

59) A further embodiment of the invention relates to a pharmaceutical composition according to embodiment 56) or 57) for use in the prevention/prophylaxis and/or treatment of a disease or disorder listed in any one of embodiments 48) to 55).

60) A further embodiment of the invention relates to a pharmaceutical composition containing, as active principle, 5H-dibenzo[b,f]azepine-5-carboxamide (Carbamazepine), (RS)-3-ethyl-3-methyl-pyrrolidine-2,5-dione (Ethosuximide), 6-(2,3-dichlorophenyl)-1,2,4-triazine-3,5-diamine (Lamotrigine), (S)-2-(2-oxopyrrolidin-1-yl)butanamide (Levetiracetam), 10,11-dihydro-10-oxo-5H-dibenz[b,f]azepine-5-carboxamide (Oxcarbazepine), 2-propylpentanoic acid (Valproic acid), N-(5-sulfamoyl-1,3,4-thiadiazol-2-yl)acetamide (Acetazolamide), (2S)-2-[(4R)-2-oxo-4-propylpyrrolidin-1-yl]butanamide (Brivaracetam), 7-chloro-1-methyl-5-phenyl-1,5-benzodiazepine-2,4-dione (Clobazam), 5-(2-chlorophenyl)-7-nitro-1,3-dihydro-1,4-benzodiazepin-2-one (Clonazepam), (S)-10-acetoxy-10,11-dihydro-5H-dibenz[b,f]azepine-5-carboxamide (Eslicarbazepine acetate), (3-carbamoyloxy-2-phenylpropyl) carbamate (Felbamate), 1-(aminomethyl)cyclohexaneacetic acid (Gabapentin), (R)-2-acetamido-N-benzyl-3-methoxypropanamide (Lacosamide), 5'-(2-cyanophenyl)-1'-phenyl-2,3'-bipyridinyl-6'(1'H)-one (Perampanel), 5-ethyl-5-phenyl-1,3-diazinane-2,4,6-trione (Phenobarbital), 5,5-diphenylimidazolidine-2,4-dione (Phenytoin), 2-(2-oxopyrrolidin-1-yl)acetamide (Piracetam), (3S)-3-(aminomethyl)-5-methylhexanoic acid (Pregabalin), 5-ethyl-5-phenyl-1,3-diazinane-4,6-dione (Primidone), ethyl (2-amino-4-((4-fluorobenzyl)amino)phenyl)carbamate (Retigabine), 1-(2,6-difluorobenzyl)-1H-1,2,3-triazole-4-carboxamide (Rufinamide), (RS)-(E)-4,4-dimethyl-1-[3,4(methylenedioxy)-phenyl]-1-penten-3-ol (Stiripentol), (3R)-1-[4,4-bis(3-methyl-2-thienyl)-3-buten-1-yl]-3-piperidinecarboxylic acid (Tiagabine), 2,3:4,5-bis-O-(1-methylethylidene)-β-D-fructopyranose sulfamate (Topiramate), (RS)-4-aminohex-5-enoic acid (Vigabatrin), or benzo[d]isoxazol-3-ylmethanesulfonamide (Zonisamide), or a pharmaceutically acceptable salt thereof, and at least one therapeutically inert excipient, wherein the pharmaceutical composition is to be administered in combination with a second pharmaceutical composition containing, as active principle, N-[1-(5-Cyano-pyridin-2-ylmethyl)-1H-pyrazol-3-yl]-2-[4-(1-trifluoromethyl-cyclopropyl)-phenyl]-acetamide, or a pharmaceutically acceptable salt thereof, and at least one therapeutically inert excipient.

61) A further embodiment of the invention relates to a pharmaceutical composition containing, as active principle, (RS)-3-ethyl-3-methyl-pyrrolidine-2,5-dione (Ethosuximide), 6-(2,3-dichlorophenyl)-1,2,4-triazine-3,5-diamine (Lamotrigine), (S)-2-(2-oxopyrrolidin-1-yl)butanamide (Levetiracetam), 2-propylpentanoic acid (Valproic acid), or 5-(2-chlorophenyl)-7-nitro-1,3-dihydro-1,4-benzodiazepin-2-one (Clonazepam), or a pharmaceutically acceptable salt thereof, and at least one therapeutically inert excipient, wherein the pharmaceutical composition is to be administered in combination with a second pharmaceutical composition containing, as active principle, N-[1-(5-Cyano-pyridin-2-ylmethyl)-1H-pyrazol-3-yl]-2-[4-(1-trifluoromethyl-cyclopropyl)-phenyl]-acetamide, or a pharmaceutically acceptable salt thereof, and at least one therapeutically inert excipient.

62) A further embodiment of the invention relates to a pharmaceutical composition according to embodiment 60) or 61) for use as a medicament.

63) A further embodiment of the invention relates to a pharmaceutical composition according to embodiment 60) or 61) for use in the prevention/prophylaxis and/or treatment of a disease or disorder listed in any one of embodiments 48) to 55).

64) A further embodiment of the invention relates to a kit of parts comprising a first pharmaceutical composition containing, as active principle, N-[1-(5-Cyano-pyridin-2-ylmethyl)-1H-pyrazol-3-yl]-2-[4-(1-trifluoromethyl-cyclopropyl)-phenyl]-acetamide, or a pharmaceutically acceptable salt thereof, and at least one therapeutically inert excipient; and a second pharmaceutical composition containing, as active principle, 5H-dibenzo[b,f]azepine-5-carboxamide (Carbamazepine), (RS)-3-ethyl-3-methyl-pyrrolidine-2,5-dione (Ethosuximide), 6-(2,3-dichlorophenyl)-1,2,4-triazine-3,5-diamine (Lamotrigine), (S)-2-(2-oxopyrrolidin-1-yl)butanamide (Levetiracetam), 10,11-dihydro-10-oxo-5H-dibenz[b,f]azepine-5-carboxamide (Oxcarbazepine), 2-propylpentanoic acid (Valproic acid), N-(5-sulfamoyl-1,3,4-thiadiazol-2-yl)acetamide (Acetazolamide), (2S)-2-[(4R)-2-oxo-4-propylpyrrolidin-1-yl]butanamide (Brivaracetam), 7-chloro-1-methyl-5-phenyl-1,5-benzodiazepine-2,4-dione (Clobazam), 5-(2-chlorophenyl)-7-nitro-1,3-dihydro-1,4-benzodiazepin-2-one (Clonazepam), (S)-10-acetoxy-10,11-dihydro-5H-dibenz[b,f]azepine-5-carboxamide (Eslicarbazepine acetate), (3-carbamoyloxy-2-phenylpropyl) carbamate (Felbamate), 1-(aminomethyl)cyclohexaneacetic acid (Gabapentin), (R)-2-acetamido-N-benzyl-3-methoxypropanamide (Lacosamide), 5'-(2-cyanophenyl)-1'-phenyl-2,3'-bipyridinyl-6'(1'H)-one (Perampanel), 5-ethyl-5-phenyl-1,3-diazinane-2,4,6-trione (Phenobarbital), 5,5-diphenylimidazolidine-2,4-dione (Phenytoin), 2-(2-oxopyrrolidin-1-yl)acetamide (Piracetam), (3S)-3-(aminomethyl)-5-methylhexanoic acid (Pregabalin), 5-ethyl-5-phenyl-1,3-diazinane-4,6-dione (Primidone), ethyl (2-amino-4-((4-fluorobenzyl)amino)phenyl)carbamate (Retigabine), 1-(2,6-difluorobenzyl)-1H-1,2,3-triazole-4-carboxamide (Rufinamide), (RS)-(E)-4,4-dimethyl-1-[3,4(methylenedioxy)-phenyl]-1-penten-3-ol (Stiripentol), (3R)-1-[4,4-bis(3-methyl-2-thienyl)-3-buten-1-yl]-3-piperidinecarboxylic acid (Tiagabine), 2,3:4,5-bis-O-(1-methylethylidene)-β-D-fructopyranose sulfamate (Topiramate), (RS)-4-aminohex-5-enoic acid (Vigabatrin), or benzo[d]isoxazol-3-ylmethanesulfonamide (Zonisamide), or a pharmaceutically acceptable salt thereof, and at least one therapeutically inert excipient.

65) A further embodiment of the invention relates to a kit of parts comprising a first pharmaceutical composition containing, as active principle, N-[1-(5-Cyano-pyridin-2-ylmethyl)-1H-pyrazol-3-yl]-2-[4-(1-trifluoromethyl-cyclopropyl)-phenyl]-acetamide, or a pharmaceutically acceptable salt thereof, and at least one therapeutically inert excipient; and a second pharmaceutical composition containing, as active principle, (RS)-3-ethyl-3-methyl-pyrrolidine-2,5-dione (Ethosuximide), 6-(2,3-dichlorophenyl)-1,2,4-triazine-3,5-diamine (Lamotrigine), (S)-2-(2-oxopyrrolidin-1-yl)butanamide (Levetiracetam), 2-propylpentanoic acid (Valproic acid), or 5-(2-chlorophenyl)-7-nitro-1,3-dihydro-1,4-benzodiazepin-2-one (Clonazepam), or a pharmaceutically acceptable salt thereof, and at least one therapeutically inert excipient.

66) A further embodiment of the invention relates to a kit of parts according to embodiment 64) or 65) further comprising instructions for the simultaneous, sequential or separate administration of the pharmaceutical compositions.

67) A further embodiment of the invention relates to a kit of parts according to any one of embodiments 64) to 66) for use as a medicament.

68) A further embodiment of the invention relates to a kit of parts according to any one of embodiments 64) to 66) for use in the prevention/prophylaxis and/or treatment of a disease or disorder listed in any one of embodiments 48) to 55).

69) A further embodiment of the invention relates to the use of N-[1-(5-Cyano-pyridin-2-ylmethyl)-1H-pyrazol-3-yl]-2-[4-(1-trifluoromethyl-cyclopropyl)-phenyl]-acetamide, or a pharmaceutically acceptable salt thereof, and a second active ingredient which is selected from the group consisting of 5H-dibenzo[b,f]azepine-5-carboxamide (Carbamazepine), (RS)-3-ethyl-3-methyl-pyrrolidine-2,5-dione (Ethosuximide), 6-(2,3-dichlorophenyl)-1,2,4-triazine-3,5-diamine (Lamotrigine), (S)-2-(2-oxopyrrolidin-1-yl)butanamide (Levetiracetam), 10,11-dihydro-10-oxo-5H-dibenz[b,f]azepine-5-carboxamide (Oxcarbazepine), 2-propylpentanoic acid (Valproic acid), N-(5-sulfamoyl-1,3,4-thiadiazol-2-yl)acetamide (Acetazolamide), (2S)-2-[(4R)-2-oxo-4-propylpyrrolidin-1-yl]butanamide (Brivaracetam), 7-chloro-1-methyl-5-phenyl-1,5-benzodiazepine-2,4-dione (Clobazam), 5-(2-chlorophenyl)-7-nitro-1,3-dihydro-1,4-benzodiazepin-2-one (Clonazepam), (S)-10-acetoxy-10,11-dihydro-5H-dibenz[b,f]azepine-5-carboxamide (Eslicarbazepine acetate), (3-carbamoyloxy-2-phenylpropyl) carbamate (Felbamate), 1-(aminomethyl)cyclohexaneacetic acid (Gabapentin), (R)-2-acetamido-N-benzyl-3-methoxypropanamide (Lacosamide), 5'-(2-cyanophenyl)-1'-phenyl-2,3'-bipyridinyl-6'(1'H)-one (Perampanel), 5-ethyl-5-phenyl-1,3-diazinane-2,4,6-trione (Phenobarbital), 5,5-diphenylimidazolidine-2,4-dione (Phenytoin), 2-(2-oxopyrrolidin-1-yl)acetamide (Piracetam), (3S)-3-(aminomethyl)-5-methylhexanoic acid (Pregabalin), 5-ethyl-5-phenyl-1,3-diazinane-4,6-dione (Primidone), ethyl (2-amino-4-((4-fluorobenzyl)amino)phenyl)carbamate (Retigabine), 1-(2,6-difluorobenzyl)-1H-1,2,3-triazole-4-carboxamide (Rufinamide), (RS)-(E)-4,4-dimethyl-1-[3,4 (methylenedioxy)-phenyl]-1-penten-3-ol (Stiripentol), (3R)-1-[4,4-bis(3-methyl-2-thienyl)-3-buten-1-yl]-3-piperidinecarboxylic acid (Tiagabine), 2,3:4,5-bis-O-(1-methylethylidene)-β-D-fructopyranose sulfamate (Topiramate), (RS)-4-aminohex-5-enoic acid (Vigabatrin), or benzo[d]isoxazol-3-ylmethanesulfonamide (Zonisamide), or a pharmaceutically acceptable salt thereof, for the manufacture of a medicament for use in the prevention/prophylaxis and/or treatment of a disease or disorder listed in any one of embodiments 48) to 55).

70) A further embodiment of the invention relates to the use according to embodiment 69), wherein the second active ingredient is (RS)-3-ethyl-3-methyl-pyrrolidine-2,5-dione (Ethosuximide), 6-(2,3-dichlorophenyl)-1,2,4-triazine-3,5-diamine (Lamotrigine), (S)-2-(2-oxopyrrolidin-1-yl)butanamide (Levetiracetam), 2-propylpentanoic acid (Valproic acid), or 5-(2-chlorophenyl)-7-nitro-1,3-dihydro-1,4-benzodiazepin-2-one (Clonazepam), or a pharmaceutically acceptable salt thereof.

71) A further embodiment of the invention relates to the use of N-[1-(5-Cyano-pyridin-2-ylmethyl)-1H-pyrazol-3-yl]-2-[4-(1-trifluoromethyl-cyclopropyl)-phenyl]-acetamide), or a pharmaceutically acceptable salt thereof, for the manufacture of a medicament for use, in combination with a second medicament comprising 5H-dibenzo[b,f]azepine-5-carboxamide (Carbamazepine), (RS)-3-ethyl-3-methyl-pyrrolidine-2,5-dione (Ethosuximide), 6-(2,3-dichlorophenyl)-1,2,4-triazine-3,5-diamine (Lamotrigine), (S)-2-(2-oxopyrrolidin-1-yl)butanamide (Levetiracetam), 10,11-dihydro-10-oxo-5H-dibenz[b,f]azepine-5-carboxamide (Oxcarbazepine), 2-propylpentanoic acid (Valproic acid), N-(5-sulfamoyl-1,3,4-thiadiazol-2-yl)acetamide (Acetazolamide), (2S)-2-[(4R)-2-oxo-4-propylpyrrolidin-1-yl]butanamide (Brivaracetam), 7-chloro-1-methyl-5-phenyl-1,5-benzodiazepine-2,4-dione (Clobazam), 5-(2-chlorophenyl)-7-nitro-1,3-dihydro-1,4-benzodiazepin-2-one (Clonazepam), (S)-10-acetoxy-10,11-dihydro-5H-dibenz[b,f]azepine-5-carboxamide (Eslicarbazepine acetate), (3-carbamoyloxy-2-phenylpropyl) carbamate (Felbamate), 1-(aminomethyl)cyclohexaneacetic acid (Gabapentin), (R)-2-acetamido-N-benzyl-3-methoxypropanamide (Lacosamide), 5'-(2-cyanophenyl)-1'-phenyl-2,3'-bipyridinyl-6'(1'H)-one (Perampanel), 5-ethyl-5-phenyl-1,3-diazinane-2,4,6-trione (Phenobarbital), 5,5-diphenylimidazolidine-2,4-dione (Phenytoin), 2-(2-oxopyrrolidin-1-yl)acetamide (Piracetam), (3S)-3-(aminomethyl)-5-methylhexanoic acid (Pregabalin), 5-ethyl-5-phenyl-1,3-diazinane-4,6-dione (Primidone), ethyl (2-amino-4-((4-fluorobenzyl)amino)phenyl)carbamate (Retigabine), 1-(2,6-difluorobenzyl)-1H-1,2,3-triazole-4-carboxamide (Rufinamide), (RS)-(E)-4,4-dimethyl-1-[3,4 (methylenedioxy)-phenyl]-1-penten-3-ol (Stiripentol), (3R)-1-[4,4-bis(3-methyl-2-thienyl)-3-buten-1-yl]-3-piperidinecarboxylic acid (Tiagabine), 2,3:4,5-bis-O-(1-methylethylidene)-β-D-fructopyranose sulfamate (Topiramate), (RS)-4-aminohex-5-enoic acid (Vigabatrin), or benzo[d]isoxazol-3-ylmethanesulfonamide (Zonisamide), or a pharmaceutically acceptable salt thereof, in the prevention/prophylaxis and/or treatment of a disease or disorder listed in any one of embodiments 48) to 55).

72) A further embodiment of the invention relates to the use according to embodiment 71), wherein the second medicament comprises (RS)-3-ethyl-3-methyl-pyrrolidine-2,5-dione (Ethosuximide), 6-(2,3-dichlorophenyl)-1,2,4-triazine-3,5-diamine (Lamotrigine), (S)-2-(2-oxopyrrolidin-1-yl)butanamide (Levetiracetam), 2-propylpentanoic acid (Valproic acid), or 5-(2-chlorophenyl)-7-nitro-1,3-dihydro-1,4-benzodiazepin-2-one (Clonazepam), or a pharmaceutically acceptable salt thereof.

73) A further embodiment of the invention relates to the use of 5H-dibenzo[b,f]azepine-5-carboxamide (Carbamazepine), (RS)-3-ethyl-3-methyl-pyrrolidine-2,5-dione (Ethosuximide), 6-(2,3-dichlorophenyl)-1,2,4-triazine-3,5-diamine (Lamotrigine), (S)-2-(2-oxopyrrolidin-1-yl)butanamide (Levetiracetam), 10,11-dihydro-10-oxo-5H-dibenz[b,f]azepine-5-carboxamide (Oxcarbazepine), 2-propylpentanoic acid (Valproic acid), N-(5-sulfamoyl-1,3,4-thiadiazol-2-yl)acetamide (Acetazolamide), (2S)-2-[(4R)-2-oxo-4-propylpyrrolidin-1-yl]butanamide (Brivaracetam), 7-chloro-1-methyl-5-phenyl-1,5-benzodiazepine-2,4-dione (Clobazam), 5-(2-chlorophenyl)-7-nitro-1,3-dihydro-1,4-benzodiazepin-2-one (Clonazepam), (S)-10-acetoxy-10,11-dihydro-5H-dibenz[b,f]azepine-5-carboxamide (Eslicarbazepine acetate), (3-carbamoyloxy-2-phenylpropyl) carbamate (Felbamate), 1-(aminomethyl)cyclohexaneacetic acid (Gabapentin), (R)-2-acetamido-N-benzyl-3-methoxypropanamide (Lacosamide), 5'-(2-cyanophenyl)-1'-phenyl-2,3'-bipyridinyl-6'(1'H)-one (Perampanel), 5-ethyl-5-phenyl-1,3-diazinane-2,4,6-trione (Phenobarbital), 5,5-diphenylimidazolidine-2,4-dione (Phenytoin), 2-(2-oxopyrrolidin-1-yl)acetamide (Piracetam), (3S)-3-(aminomethyl)-5-methylhexanoic acid (Pregabalin), 5-ethyl-5-phenyl-1,3-diazinane-4,6-dione (Primidone), ethyl (2-amino-4-((4-fluorobenzyl)amino)phenyl)carbamate (Retigabine), 1-(2,6-difluorobenzyl)-1H-1,2,3-triazole-4-carboxamide (Rufinamide), (RS)-(E)-4,4-dimethyl-1-[3,4 (methylenedioxy)-phenyl]-1-penten-3-ol (Stiripentol), (3R)-1-[4,4-bis(3-methyl-2-thienyl)-3-buten-1-yl]-3-piperidinecarboxylic acid (Tiagabine), 2,3:4,5-bis-O-(1-methylethylidene)-β-D-fructopyranose sulfamate (Topiramate), (RS)-4-aminohex-5-enoic acid (Vigabatrin), or benzo[d]isoxazol-3-ylmethanesulfonamide (Zonisamide), or a pharmaceutically acceptable salt thereof, for the manufacture of a medicament for use, in combination with a second medicament comprising N-[1-(5-Cyano-pyridin-2-ylmethyl)-1H-pyrazol-3-yl]-2-[4-(1-trifluoromethyl-cyclopropyl)-phenyl]-acetamide, or a pharmaceutically acceptable salt thereof, in the prevention/prophylaxis and/or treatment of a disease or disorder listed in any one of embodiments 48) to 55).

74) A further embodiment of the invention relates to the use of (RS)-3-ethyl-3-methyl-pyrrolidine-2,5-dione (Ethosuximide), 6-(2,3-dichlorophenyl)-1,2,4-triazine-3,5-diamine (Lamotrigine), 2-propylpentanoic acid (Valproic acid), or 5-(2-chlorophenyl)-7-nitro-1,3-dihydro-1,4-benzodiazepin-2-one (Clonazepam), or a pharmaceutically acceptable salt thereof, for the manufacture of a medicament for use, in combination with a second medicament comprising N-[1-(5-Cyano-pyridin-2-ylmethyl)-1H-pyrazol-3-yl]-2-[4-(1-trifluoromethyl-cyclopropyl)-phenyl]-acetamide, or a pharmaceutically acceptable salt thereof, in the prevention/prophylaxis and/or treatment of a disease or disorder listed in any one of embodiments 48) to 55).

Based on the dependencies of the different embodiments 1) to 74) as disclosed hereinabove, the following embodiments are thus possible and intended and herewith specifically disclosed in individualised form: 1, 2+1, 3+1, 4+1, 5+1, 6+1, 7+1, 8+1, 9+1, 10+1, 11+1, 12+1, 13+1, 14+1, 15+1, 16+1, 17+1, 18+1, 19+1, 20+1, 21+1, 22+1, 23+1, 24+1, 25+1, 26+1, 27+1, 28+1, 29+1, 30+1, 31+1, 32+1, 33+1, 34+1, 35+1, 36+1, 37+1, 38+1, 39+1, 40+1, 41+1, 42+1, 43+1, 44+1, 45+1, 45+2+1, 45+3+1, 45+4+1, 45+5+1, 45+6+1, 45+7+1, 45+8+1, 45+9+1, 45+10+1, 45+11+1, 45+12+1, 45+13+1, 45+14+1, 45+15+1, 45+16+1, 45+17+1, 45+18+1, 45+19+1, 45+20+1, 45+21+1, 45+22+1, 45+23+1, 45+24+1, 45+25+1, 45+26+1, 45+27+1, 45+28+1, 45+29+1, 45+30+1, 45+31+1, 45+32+1, 45+33+1, 45+34+1, 45+35+1, 45+36+1, 45+37+1, 45+38+1, 45+39+1, 45+40+1, 45+41+1, 45+42+1, 45+43+1, 45+44+1, 46+1, 46+2+1, 46+3+1, 46+4+1, 46+5+1, 46+6+1, 46+7+1, 46+8+1, 46+9+1, 46+10+1, 46+11+1, 46+12+1, 46+13+1, 46+14+1, 46+15+1, 46+16+1, 46+17+1, 46+18+1, 46+19+1, 46+20+1, 46+21+1, 46+22+1, 46+23+1, 46+24+1, 46+25+1, 46+26+1, 46+27+1, 46+28+1, 46+29+1, 46+30+1, 46+31+1, 46+32+1, 46+33+1, 46+34+1, 46+35+1, 46+36+1, 46+37+1, 46+38+1, 46+39+1, 46+40+1, 46+41+1, 46+42+1, 46+43+1, 46+44+1, 47+1, 47+2+1, 47+3+1, 47+4+1, 47+5+1, 47+6+1, 47+7+1, 47+8+1, 47+9+1, 47+10+1, 47+11+1, 47+12+1, 47+13+1, 47+14+1, 47+15+1, 47+16+1, 47+17+1, 47+18+1, 47+19+1, 47+20+1, 47+21+1, 47+22+1, 47+23+1, 47+24+1, 47+25+1, 47+26+1, 47+27+1, 47+28+1, 47+29+1, 47+30+1, 47+31+1, 47+32+1, 47+33+1, 47+34+1, 47+35+1, 47+36+1, 47+37+1, 47+38+1, 47+39+1, 47+40+1, 47+41+1, 47+42+1, 47+43+1, 47+44+1, 47+45+1, 47+45+2+1, 47+45+3+1, 47+45+4+1, 47+45+5+1, 47+45+6+1, 47+45+7+1, 47+45+8+1, 47+45+9+1, 47+45+10+1, 47+45+11+1, 47+45+12+1, 47+45+13+1, 47+45+14+1, 47+45+15+1, 47+45+16+1, 47+45+17+1, 47+45+18+1, 47+45+19+1, 47+45+20+1, 47+45+21+1, 47+45+22+1, 47+45+23+1, 47+45+24+1, 47+45+25+1, 47+45+26+1, 47+45+27+1, 47+45+28+1, 47+45+29+1, 47+45+30+1, 47+45+31+1, 47+45+32+1, 47+45+33+1, 47+45+34+1, 47+45+35+1, 47+45+36+1, 47+45+37+1, 47+45+38+1, 47+45+39+1, 47+45+40+1, 47+45+41+1, 47+45+42+1, 47+45+43+1, 47+45+44+1, 47+46+1, 47+46+2+1, 47+46+3+1, 47+46+4+1, 47+46+5+1, 47+46+6+1, 47+46+7+1, 47+46+8+1, 47+46+9+1, 47+46+10+1, 47+46+11+1, 47+46+12+1, 47+46+13+1, 47+46+14+1, 47+46+15+1, 47+46+16+1, 47+46+17+1, 47+46+18+1, 47+46+19+1, 47+46+20+1, 47+46+21+1, 47+46+22+1, 47+46+23+1, 47+46+24+1, 47+46+25+1, 47+46+26+1, 47+46+27+1, 47+46+28+1, 47+46+29+1, 47+46+30+1, 47+46+31+1, 47+46+32+1, 47+46+33+1, 47+46+34+1, 47+46+35+1, 47+46+36+1, 47+46+37+1, 47+46+38+1, 47+46+39+1, 47+46+40+1, 47+46+41+1, 47+46+42+1, 47+46+43+1, 47+46+44+1, 48+1, 48+2+1, 48+3+1, 48+4+1, 48+5+1, 48+6+1, 48+7+1, 48+8+1, 48+9+1, 48+10+1, 48+11+1, 48+12+1, 48+13+1, 48+14+1, 48+15+1, 48+16+1, 48+1+1, 48+18+8+1, 48+19+1, 48+20+1, 48+21+1, 48+22+1, 48+23+1, 48+24+1, 48+25+1, 48+26+1, 48+27+1, 48+28+1, 48+29+1, 48+30+1, 48+31+1, 48+32+1, 48+33+1, 48+34+1, 48+35+1, 48+36+1, 48+37+1, 48+38+1, 48+39+1, 48+40+1, 48+41+1, 48+42+1, 48+43+1, 48+44+1, 48+45+1, 48+45+2+1, 48+45+3+1, 48+45+4+1, 48+45+5+1, 48+45+6+1, 48+45+7+1, 48+45+8+1, 48+45+9+1, 48+45+10+1, 48+45+11+1, 48+45+12+1, 48+45+13+1, 48+45+14+1, 48+45+15+1, 48+45+16+1, 48+45+17+1, 48+45+18+1, 48+45+19+1, 48+45+20+1, 48+45+21+1, 48+45+22+1, 48+45+23+1, 48+45+24+1, 48+45+25+1, 48+45+26+1, 48+45+27+1, 48+45+28+1, 48+45+29+1, 48+45+30+1, 48+45+31+1, 48+45+32+1, 48+45+33+1, 48+45+34+1, 48+45+35+1, 48+45+36+1, 48+45+37+1, 48+45+38+1, 48+45+39+1, 48+45+40+1, 48+45+41+1, 48+45+42+1, 48+45+43+1, 48+45+44+1, 48+46+1, 48+46+2+1, 48+46+3+1, 48+46+4+1, 48+46+5+1, 48+46+6+1, 48+46+7+1, 48+46+8+1, 48+46+9+1, 48+46+10+1, 48+46+11+1, 48+46+12+1, 48+46+13+1, 48+46+14+1, 48+46+15+1, 48+46+16+1, 48+46+17+1, 48+46+18+1, 48+46+19+1, 48+46+20+1, 48+46+21+1, 48+46+22+1, 48+46+23+1, 48+46+24+1, 48+46+25+1, 48+46+26+1, 48+46+27+1, 48+46+28+1, 48+46+29+1, 48+46+30+1, 48+46+31+1, 48+46+32+1, 48+46+33+1, 48+46+34+1, 48+46+35+1, 48+46+36+1, 48+46+37+1, 48+46+38+1, 48+46+39+1, 48+46+40+1, 48+46+41+1, 48+46+42+1, 48+46+43+1, 48+46+44+1, 49+1, 49+2+1, 49+3+1, 49+4+1, 49+5+1, 49+6+1, 49+7+1, 49+8+1, 49+9+1, 49+10+1, 49+11+1, 49+12+1, 49+13+1, 49+14+1, 49+15+1, 49+16+1, 49+17+1, 49+18+1, 49+19+1, 49+20+1, 49+21+1, 49+22+1, 49+23+1, 49+24+1, 49+25+1, 49+26+1, 49+27+1, 49+28+1, 49+29+1, 49+30+1, 49+31+1, 49+32+1, 49+33+1, 49+34+1, 49+35+1, 49+36+1, 49+37+1, 49+38+1, 49+39+1, 49+40+1, 49+41+1, 49+42+1, 49+43+1, 49+44+1, 49+45+1, 49+45+2+1, 49+45+3+1, 49+45+4+1, 49+45+5+1, 49+45+6+1, 49+45+7+1, 49+45+8+1, 49+45+9+1, 49+45+10+1, +49+45+11+1, +49+45+12+1, 49+45+13+1, 49+45+14+1, 49+45+15+1, 49+45+16+1, 49+45+17+1, 49+45+18+1, 49+45+19+1, 49+45+20+1, 49+45+21+1, 49+45+22+1, 49+45+23+1, 49+45+24+1, 49+45+25+1, 49+45+26+1, 49+45+27+1, 49+45+28+1, 49+45+29+1, 49+45+30+1, 49+45+31+1, 49+45+32+1, 49+45+33+1, 49+45+34+1, 49+45+35+1, 49+45+36+1, 49+45+37+1, 49+45+38+1, 49+45+39+1, 49+45+40+1, 49+45+41+1, 49+45+42+1, 49+45+43+1, 49+45+44+1, 49+46+1, 49+46+2+1, 49+46+3+1, 49+46+4+1, 49+46+5+1, 49+46+6+1, 49+46+7+1, 49+46+8+1, 49+46+9+1, 49+46+10+1, 49+46+11+1, 49+46+12+1, 49+46+13+1, 49+46+14+1, 49+46+15+1, 49+46+16+1, 49+46+17+1, 49+46+18+1, 49+46+19+1, 49+46+20+1, 49+46+21+1, 49+46+22+1, 49+46+23+1, 49+46+24+1, 49+46+25+1, 49+46+26+1, 49+46+27+1, 49+46+28+1, 49+46+29+1, 49+46+30+1, 49+46+31+1, 49+46+32+1, 49+46+33+1, 49+46+34+1, 49+46+35+1, 49+46+36+1, 49+46+37+1, 49+46+38+1, 49+46+39+1, 49+46+40+1, 49+46+41+1, 49+46+42+1, 49+46+43+1, 49+46+44+1, 50+1, 50+2+1, 50+3+1, 50+4+1, 50+5+1, 50+6+1, 50+7+1, 50+8+1, 50+9+1, 50+10+1, 50+11+1, 50+12+1, 50+13+1, 50+14+1, 50+15+1, 50+16+1, 50+17+1, 50+18+1, 50+19+1, 50+20+1, 50+21+1, 50+22+1, 50+23+1, 50+24+1, 50+25+1, 50+26+1, 50+27+1, 50+28+1, 50+29+1, 50+30+1, 50+31+1, 50+32+1, 50+33+1, 50+34+1, 50+35+1, 50+36+1, 50+37+1, 50+38+1, 50+39+1, 50+40+1, 50+41+1, 50+42+

1, 50+43+1, 50+44+1, 50+45+1, 50+45+2+1, 50+45+3+1, 50+45+4+1, 50+45+5+1, 50+45+6+1, 50+45+7+1, 50+45+8+1, 50+45+9+1, 50+45+10+1, 50+45+11+1, 50+45+12+1, 50+45+13+1, 50+45+14+1, 50+45+15+1, 50+45+16+1, 50+45+17+1, 50+45+18+1, 50+45+19+1, 50+45+20+1, 50+45+21+1, 50+45+22+1, 50+45+23+1, 50+45+24+1, 50+45+25+1, 50+45+26+1, 50+45+27+1, 50+45+28+1, 50+45+29+1, 50+45+30+1, 50+45+31+1, 50+45+32+1, 50+45+33+1, 50+45+34+1, 50+45+35+1, 50+45+36+1, 50+45+37+1, 50+45+38+1, 50+45+39+1, 50+45+40+1, 50+45+41+1, 50+45+42+1, 50+45+43+1, 50+45+44+1, 50+46+1, 50+46+2+1, 50+46+3+1, 50+46+4+1, 50+46+5+1, 50+46+6+1, 50+46+7+1, 50+46+8+1, 50+46+9+1, 50+46+10+1, 50+46+11+1, 50+46+12+1, 50+46+13+1, 50+46+14+1, 50+46+15+1, 50+46+16+1, 50+46+17+1, 50+46+18+1, 50+46+19+1, 50+46+20+1, 50+46+20+1, 50+46+21+1, 50+46+22+1, 50+46+23+1, 50+46+24+1, 50+46+25+1, 50+46+26+1, 50+46+27+1, 50+46+28+1, 50+46+29+1, 50+46+30+1, 50+46+31+1, 50+46+32+1, 50+46+33+1, 50+46+34+1, 50+46+35+1, 50+46+36+1, 50+46+37+1, 50+46+38+1, 50+46+39+1, 50+46+40+1, 50+46+41+1, 50+46+42+1, 50+46+43+1, 50+46+44+1, 51+1, 51+2+1, 51+3+1, 51+4+1, 51+5+1, 51+6+1, 51+7+1, 51+8+1, 51+9+1, 51+10+1, 51+11+1, 51+12+1, 51+13+1, 51+14+1, 51+15+1, 51+16+1, 51+17+1, 51+18+1, 51+19+1, 51+20+1, 51+21+1, 51+22+1, 51+23+1, 51+24+1, 51+25+1, 51+26+1, 51+27+1, 51+28+1, 51+29+1, 51+30+1, 51+31+1, 51+32+1, 51+33+1, 51+34+1, 51+35+1, 51+36+1, 51+37+1, 51+38+1, 51+39+1, 51+40+1, 51+41+1, 51+42+1, 51+43+1, 51+44+1, 51+45+1, 51+45+2+1, 51+45+3+1, 51+45+4+1, 51+45+5+1, 51+45+6+1, 51+45+7+1, 51+45+8+1, 51+45+9+1, 51+45+10+1, 51+45+11+1, 51+45+12+1, 51+45+13+1, 51+45+14+1, 51+45+15+1, 51+45+16+1, 51+45+17+1, 51+45+18+1, 51+45+19+1, 51+45+20+1, 51+45+21+1, 51+45+22+1, 51+45+19+1, 51+45+20+1, 51+45+21+1, 51+45+23+1, +24+1, 51+45+25+1, 51+45+26+1, 51+45+27+1, 51+45+28+1, 51+45+29+1, 51+45+30+1, 51+45+31+1, 51+45+32+1, 51+45+33+1, 51+45+34+1, 51+45+35+1, 51+45+36+1, 51+45+37+1, 51+45+38+1, 51+45+39+1, 51+45+40+1, 51+45+41+1, 51+45+42+1, 51+45+43+1, 51+45+44+1, 51+46+1, 51+46+2+1, 51+46+3+1, 51+46+4+1, 51+46+5+1, 51+46+6+1, 51+46+7+1, 51+46+8+1, 51+46+9+1, 51+46+10+1, 51+46+11+1, 51+46+12+1, 51+46+13+1, 51+46+14+1, 51+46+15+1, 51+46+16+1, 51+46+17+1, 51+46+18+1, 51+46+19+1, 51+46+20+1, 51+46+21+1, 51+46+22+1, 51+46+23+1, 51+46+24+1, 51+46+25+1, 51+46+26+1, 51+46+27+1, 51+46+28+1, 51+46+29+1, 51+46+30+1, 51+46+31+1, 51+46+32+1, 51+46+33+1, 51+46+34+1, 51+46+35+1, 51+46+36+1, 51+46+37+1, 51+46+38+1, 51+46+39+1, 51+46+40+1, 51+46+41+1, 51+46+42+1, 51+46+43+1, 51+46+44+1, 52+1, 52+2+1, 52+3+1, 52+4+1, 52+5+1, 52+6+1, 52+7+1, 52+8+1, 52+9+1, 52+10+1, 52+11+1, 52+12+1, 52+13+1, 52+14+1, 52+15+1, 52+16+1, 52+17+1, 52+18+1, 52+19+1, 52+20+1, 52+21+1, 52+22+1, 52+23+1, 52+24+1, 52+25+1, 52+26+1, 52+27+1, 52+28+1, 52+29+1, 52+30+1, 52+31+1, 52+32+1, 52+33+1, 52+34+1, 52+35+1, 52+36+1, 52+37+1, 52+38+1, 52+39+1, 52+40+1, 52+41+1, 52+42+1, 52+43+1, 52+44+1, 52+45+1, 52+45+2+1, 52+45+3+1, 52+45+4+1, 52+45+5+1, 52+45+6+1, 52+45+7+1, 52+45+8+1, 52+45+9+1, 52+45+10+1, 52+45+11+1, 52+45+12+1, 52+45+13+1, 52+45+14+1, 52+45+15+1, 52+45+16+1, 52+45+17+1, 52+45+18+1, 52+45+19+1, 52+45+20+1, 52+45+21+1, 52+45+22+1, 52+45+23+1, 52+45+24+1, 52+45+25+1, 52+45+26+1, 52+45+27+1, 52+45+28+1, 52+45+29+1, 52+45+30+1, 52+45+31+1, 52+45+32+1, 52+45+33+1, 52+45+34+1, 52+45+35+1, 52+45+36+1, 52+45+37+1, 52+45+38+1, 52+45+39+1, 52+45+40+1, 52+45+41+1, 52+45+42+1, 52+45+43+1, 52+45+44+1, 52+46+1, 52+46+2+1, 52+46+3+1, 52+46+4+1, 52+46+5+1, 52+46+6+1, 52+46+7+1, 52+46+8+1, 52+46+9+1, 52+46+10+1, 52+46+11+1, 52+46+12+1, 52+46+13+1, 52+46+14+1, 52+46+15+1, 52+46+16+1, 52+46+17+1, 52+46+18+1, 52+46+19+1, 52+46+20+1, 52+46+21+1, 52+46+22+1, 52+46+23+1, 52+46+24+1, 52+46+25+1, 52+46+26+1, 52+46+27+1, 52+46+28+1, 52+46+29+1, 52+46+30+1, 52+46+31+1, +32+6+32+1, 52+46+33+1, 52+46+34+1, 52+46+35+1, 52+46+36+1, 52+46+37+1, 52+46+38+1, 52+46+39+1, 52+46+40+1, 52+46+41+1, 52+46+42+1, 52+46+43+1, 52+46+44+1, 53+1, 53+2+1, 53+3+1, 53+4+1, 53+5+1, 53+6+1, 53+7+1, 53+8+1, 53+9+1, 53+10+1, 53+11+1, 53+12+1, 53+13+1, 53+14+1, 53+15+1, 53+16+1, 53+17+1, 53+18+1, 53+19+1, 53+20+1, 53+21+1, 53+22+1, 53+23+1, 53+24+1, 53+25+1, 53+26+1, 53+27+1, 53+28+1, 53+29+1, 53+30+1, 53+31+1, 53+32+1, 53+33+1, 53+34+1, 53+35+1, 53+36+1, 53+37+1, 53+38+1, 53+39+1, 53+40+1, 53+41+1, 53+42+1, 53+43+1, 53+44+1, 53+45+1, 53+45+2+1, 53+45+3+1, 53+45+4+1, 53+45+5+1, 53+45+6+1, 53+45+7+1, 53+45+8+1, 53+45+9+1, 53+45+10+1, 53+45+11+1, 53+45+12+1, 53+45+13+1, 53+45+14+1, 53+45+15+1, 53+45+16+1, 53+45+17+1, 53+45+18+1, 53+45+19+1, 53+45+20+1, 53+45+21+1, 53+45+22+1, 53+45+23+1, 53+45+24+1, 53+45+25+1, 53+45+26+1, 53+45+27+1, 53+45+28+1, 53+45+29+1, 53+45+30+1, 53+45+31+1, 53+45+32+1, 53+45+33+1, 53+45+34+1, 53+45+35+1, 53+45+36+1, 53+45+35+17+1, 53+45+38+1, 53+45+39+1, 53+45+40+1, 53+45+41+1, 53+45+42+1, 53+45+43+1, 53+45+44+1, 53+46+1, 53+46+2+1, 53+46+3+1, 53+46+4+1, 53+46+5+1, 53+46+6+1, 53+46+7+1, 53+46+8+1, 53+46+9+1, 53+46+10+1, 53+46+11+1, 53+46+12+1, 53+46+13+1, 53+46+14+1, 53+46+15+1, 53+46+16+1, 53+46+17+1, 53+46+18+1, 53+46+19+1, 53+46+20+1, 53+46+21+1, 53+46+22+1, 53+46+23+1, 53+46+24+1, 53+46+25+1, 53+46+26+1, 53+46+27+1, 53+46+28+1, 53+46+29+1, 53+46+30+1, 53+46+31+1, 53+46+32+1, 53+46+33+1, 53+46+34+1, 53+46+35+1, 53+46+36+1, 53+46+37+1, 53+46+38+1, 53+46+39+1, 53+46+40+1, 53+46+41+1, 53+46+42+1, 53+46+43+1, 53+46+44+1, 54+1, 54+2+1, 54+3+1, 54+4+1, 54+5+1, 54+6+1, 54+7+1, 54+8+1, 54+9+1, 54+10+1, 54+11+1, 54+12+1, 54+13+1, 54+14+1, 54+15+1, 54+16+1, 54+17+1, 54+18+1, 54+19+1, 54+20+1, 54+21+1, 54+22+1, 54+23+1, 54+24+1, 54+25+1, 54+26+1, 54+27+1, 54+28+1, 54+29+1, 54+30+1, 54+31+1, 54+32+1, 54+33+1, 54+34+1, 54+35+1, 54+36+1, 54+37+1, 54+38+1, 54+39+1, 54+40+1, 54+41+1, 54+42+1, 54+43+1, 54+44+1, 54+45+1, 54+45+2+1, 54+45+3+1, 54+45+4+1, 54+45+5+1, 54+45+6+1, 54+45+7+1, 54+45+8+1, 54+45+9+1, 54+45+10+1, 54+45+11+1, 54+45+12+1, 54+45+13+1, 54+45+14+1, 54+45+15+1, 54+45+16+1, 54+45+17+1, 54+45+18+1, 54+45+19+1, 54+45+20+1, 54+45+21+1, 54+45+22+1, 54+45+23+1, 54+45+24+1, 54+45+25+1, 54+45+26+1, 54+45+27+1, 54+45+28+1, 54+45+29+1, 54+45+30+1, 54+45+31+1, 54+45+32+1, 54+45+33+1, 54+45+34+1, 54+45+35+1, 54+45+36+1, 54+45+37+1, 54+45+38+1, 54+45+39+1, 54+45+40+1, 54+45+41+1, 54+45+42+1, 54+45+43+1, 54+45+44+1, 54+46+1, 54+46+2+1, 54+46+3+1, 54+46+4+1, 54+46+5+1, 54+46+6+1, 54+46+7+1, 54+46+8+1, 54+46+9+1, 54+46+10+1, 54+46+11+1, 54+46+12+1, 54+46+13+1, 54+46+14+1, 54+46+15+1, 54+46+16+1, 54+46+17+1, 54+46+18+1, 54+46+19+1, 54+46+20+1, 54+46+21+1, 54+46+22+1, 54+46+23+1, 54+46+24+1, 54+46+25+1, 54+46+26+1, 54+46+27+1,

54+46+28+1, 54+46+29+1, 54+46+30+1, 54+46+31+1, 54+46+32+1, 54+46+33+1, 54+46+34+1, 54+46+35+1, 54+46+36+1, 54+46+37+1, 54+46+38+1, 54+46+39+1, 54+46+40+1, 54+46+41+1, 54+46+42+1, 54+46+43+1, 54+46+44+1, 55+1, 55+2+1, 55+3+1, 55+4+1, 55+5+1, 55+6+1, 55+7+1, 55+8+1, 55+9+1, 55+10+1, 55+11+1, 55+12+1, 55+13+1, 55+14+1, 55+15+1, 55+16+1, 55+17+1, 55+18+1, 55+19+1, 55+20+1, 55+21+1, 55+22+1, 55+23+1, 55+24+1, 55+25+1, 55+26+1, 55+27+1, 55+28+1, 55+29+1, 55+30+1, 55+31+1, 55+32+1, 55+33+1, 55+34+1, 55+35+1, 55+36+1, 55+37+1, 55+38+1, 55+39+1, 55+40+1, 55+41+1, 55+42+1, 55+43+1, 55+44+1, 55+45+1, 55+45+2+1, 55+45+3+1, 55+45+4+1, 55+45+5+1, 55+45+6+1, 55+45+7+1, 55+45+8+1, 55+45+9+1, 55+45+10+1, 55+45+11+1, 55+45+12+1, 55+45+13+1, 55+45+14+1, 55+45+15+1, 55+45+16+1, 55+45+17+1, 55+45+18+1, 55+45+19+1, 55+45+20+1, 55+45+21+1, 55+45+22+1, 55+45+23+1, 55+45+24+1, 55+45+25+1, 55+45+26+1, 55+45+27+1, 55+45+28+1, 55+45+29+1, 55+45+30+1, 55+45+31+1, 55+45+32+1, 55+45+33+1, 55+45+34+1, 55+45+35+1, 55+45+36+1, 55+45+37+1, 55+45+38+1, 55+45+39+1, 55+45+40+1, 55+45+41+1, 55+45+42+1, 55+45+43+1, 55+45+44+1, 55+46+1, 55+46+2+1, 55+46+3+1, 55+46+4+1, 55+46+5+1, 55+46+6+1, 55+46+7+1, 55+46+8+1, 55+46+9+1, 55+46+10+1, 55+46+11+1, 55+46+12+1, 55+46+13+1, 55+46+14+1, 55+46+15+1, 55+46+16+1, 55+46+17+1, 55+46+18+1, 55+46+19+1, 55+46+20+1, 55+46+21+1, 55+46+22+1, 55+46+23+1, 55+46+24+1, 55+46+25+1, 55+46+26+1, 55+46+27+1, 55+46+28+1, 55+46+29+1, 55+46+30+1, 55+46+31+1, 55+46+32+1, 55+46+33+1, 55+46+34+1, 55+46+35+1, 55+46+36+1, 55+46+37+1, 55+46+38+1, 55+46+39+1, 55+46+40+1, 55+46+41+1, 55+46+42+1, 55+46+43+1, 55+46+44+1, 56, 57, 58, 59, 60, 61, 62, 63, 64, 65, 66+64, 66+65, 67, 68, 69, 70+69, 71, 72+71, 73, and 74;

In the list above the numbers refer to the embodiments according to their numbering provided hereinabove whereas "+" indicates the dependency from another embodiment. The different individualised embodiments are separated by commas. In other words, "45+2+1" for example refers to embodiment 45) depending on embodiment 2), depending on embodiment 1), i.e. embodiment "45+2+1" corresponds to the pharmaceutical combination of embodiment 45) further limited by the features of the embodiments 2) and 45).

Definitions provided herein are intended to apply uniformly to the subject matter as defined in any one of embodiments 1) to 74), and, mutatis mutandis, throughout the description and the claims unless an otherwise expressly set out definition provides a broader or narrower definition. It is well understood that a definition or preferred definition of a term or expression defines and may replace the respective term or expression independently of (and in combination with) any definition or preferred definition of any or all other terms or expressions as defined herein.

Any reference to an active ingredient as defined in any one of embodiments 1) to 74) is to be understood as referring also to the pharmaceutically acceptable salts of such active ingredient, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example 'Handbook of Pharmaceutical Salts. Properties, Selection and Use.', P. Heinrich Stahl, Camille G. Wermuth (Eds.), Wiley-VCH, 2008 and 'Pharmaceutical Salts and Co-crystals', Johan Wouters and Luc Quéré (Eds.), RSC Publishing, 2012.

The term "pharmaceutical combination", as used herein, refers to a combination of two or more, preferably two, active ingredients, wherein the active ingredients are comprised in a single pharmaceutical composition or in separated pharmaceutical compositions.

The term "active ingredient", as used herein, refers to the pharmaceutically active component of a pharmaceutical composition. Examples of active ingredients, as used herein, are in a first group N-[1-(5-Cyano-pyridin-2-ylmethyl)-1H-pyrazol-3-yl]-2-[4-(1-trifluoromethyl-cyclopropyl)-phenyl]-acetamide (COMPOUND 1), or a pharmaceutically acceptable salt thereof, and in a second group 5H-dibenzo[b,f]azepine-5-carboxamide (Carbamazepine), (RS)-3-ethyl-3-methyl-pyrrolidine-2,5-dione (Ethosuximide), 6-(2,3-dichlorophenyl)-1,2,4-triazine-3,5-diamine (Lamotrigine), (S)-2-(2-oxopyrrolidin-1-yl)butanamide (Levetiracetam), 10,11-dihydro-10-oxo-5H-dibenz[b,f]azepine-5-carboxamide (Oxcarbazepine), 2-propylpentanoic acid (Valproic acid), N-(5-sulfamoyl-1,3,4-thiadiazol-2-yl)acetamide (Acetazolamide), (2S)-2-[(4R)-2-oxo-4-propylpyrrolidin-1-yl]butanamide (Brivaracetam), 7-chloro-1-methyl-5-phenyl-1,5-benzodiazepine-2,4-dione (Clobazam), 5-(2-chlorophenyl)-7-nitro-1,3-dihydro-1,4-benzodiazepin-2-one (Clonazepam), (S)-10-acetoxy-10,11-dihydro-5H-dibenz[b,f]azepine-5-carboxamide (Eslicarbazepine acetate), (3-carbamoyloxy-2-phenylpropyl) carbamate (Felbamate), 1-(aminomethyl)cyclohexaneacetic acid (Gabapentin), (R)-2-acetamido-N-benzyl-3-methoxypropanamide (Lacosamide), 5'-(2-cyanophenyl)-1'-phenyl-2,3'-bipyridinyl-6'(1'H)-one (Perampanel), 5-ethyl-5-phenyl-1,3-diazinane-2,4,6-trione (Phenobarbital), 5,5-diphenylimidazolidine-2,4-dione (Phenytoin), 2-(2-oxopyrrolidin-1-yl)acetamide (Piracetam), (3S)-3-(aminomethyl)-5-methylhexanoic acid (Pregabalin), 5-ethyl-5-phenyl-1,3-diazinane-4,6-dione (Primidone), ethyl (2-amino-4-((4-fluorobenzyl)amino)phenyl)carbamate (Retigabine), 1-(2,6-difluorobenzyl)-1H-1,2,3-triazole-4-carboxamide (Rufinamide), (RS)-(E)-4,4-dimethyl-1-[3,4(methylenedioxy)-phenyl]-1-penten-3-ol (Stiripentol), (3R)-1-[4,4-bis(3-methyl-2-thienyl)-3-buten-1-yl]-3-piperidinecarboxylic acid (Tiagabine), 2,3:4,5-bis-O-(1-methylethylidene)-β-D-fructopyranose sulfamate (Topiramate), (RS)-4-aminohex-5-enoic acid (Vigabatrin), or benzo[d]isoxazol-3-ylmethanesulfonamide (Zonisamide), or a pharmaceutically acceptable salt thereof. For the sake of clarity, an "active ingredient which has an anti-epileptic effect" is an active ingredient that can be used in the prevention/prophylaxis and/or treatment of epileptic seizures in a patient by partially or totally suppressing clinical or electrographic signs of seizures.

The term "simultaneous" or "simultaneously", when used in relation to the administration of active ingredients or of pharmaceutical compositions, means that the administration of a first active ingredient (or of a first pharmaceutical composition, respectively) is still ongoing when the administration of a second active ingredient (or of a second pharmaceutical composition, respectively) is started. Especially, the term "simultaneous" or "simultaneously" means that two active ingredients (or two pharmaceutical compositions, respectively) are administered at the same time, i.e. with the same starting and end time, as is for instance the case for the administration of two active ingredients comprised in a single pharmaceutical composition.

The term "sequential" or "sequentially", when used in relation to the administration of active ingredients or of pharmaceutical compositions, means that the administration of a second active ingredient (or of a second pharmaceutical composition, respectively) is started less than one hour after the administration of a first active ingredient (or of a first pharmaceutical composition, respectively) has been finalized.

The term "separate" or "separately", when used in relation to the administration of active ingredients or of pharmaceutical compositions, means that the administration of a second active ingredient (or of a second pharmaceutical composition, respectively) is started one hour or more (and up to about twelve hours, or up to about 24 hours) after the last preceding administration of a first active ingredient (or of a first pharmaceutical composition, respectively) has been finalized.

The expressions "to be administered in combination" or "for use, in combination" mean simultaneous, sequential or separate, preferably sequential, administration of active ingredients or pharmaceutical compositions.

The term "route of administration", as used herein, refers to the path by which an active ingredient (e.g. in form of a pharmaceutical composition in a particular dosage form) enters the body. The active ingredients may be administered by enteral (especially oral) or parenteral administration (including topical application or inhalation). Examples of dosage forms which may be used for the administration of the active ingredients are tablets, capsules, pills, granules, powders, solutions, suspensions, emulsions, injectable aqueous or oily solutions or suspensions, suppositories, creams, gels, ear or eye drops, nasal spray, skin patches, or aerosols. Dosage forms for oral administration, such as tablets, capsules, pills, solutions or suspensions are preferred. In case the two active ingredients are comprised in separated pharmaceutical compositions, said separated pharmaceutical compositions may be administered by the same or different routes of administration using the same or different dosage forms.

The production of pharmaceutical compositions can be effected in a manner which will be familiar to any person skilled in the art (see for example Remington, The Science and Practice of Pharmacy, 21st Edition (2005), Part 5, "Pharmaceutical Manufacturing" [published by Lippincott Williams & Wilkins]) by bringing COMPOUND 1 or a pharmaceutically acceptable salt thereof and/or a second active ingredient which has an anti-epileptic effect, as defined in any one of embodiments 1) to 44), or a pharmaceutically acceptable salt thereof, optionally in combination with other therapeutically valuable substances, into a galenical administration form together with suitable, non-toxic, inert, therapeutically compatible solid or liquid carrier materials and, if desired, usual pharmaceutical adjuvants.

The optimal dosing regimen (i.e., the magnitude of the dose and the dosing frequency) for each of the two active ingredients of the pharmaceutical combination according to the present invention may vary depending upon the route of administration, the dosage form, the type of epilepsy to be treated, and the particular second active ingredient applied. Further, the dose and/or the dosing frequency may be different during the initial phase and the later phase of the treatment for the first and/or the second active ingredient of the pharmaceutical combination. Usually the treatment starts with low dose which is up-titrated during a period which varies for each anti-epileptic drug and continues with a maintenance dose that is typically adapted for each patient and should be the lowest dose that provides seizure freedom (Perucca E et al. (2011) The pharmacological treatment of epilepsy in adults. Lancet Neurol 10:446-456; Goldenberg M M (2010) Overview of Drugs Used For Epilepsy and Seizures. Pharmacy and Therapeutics 35(7): 392-415). A preferred maintenance dose for COMPOUND 1 is 5 to 600 mg orally once daily, especially 10 to 400 mg (preferred 20 to 400 mg) orally once daily, and notably 10 to 200 mg (preferred 40 to 200 mg) orally once daily.

The present invention also includes isotopically labelled, especially $^2$H (deuterium) labelled active ingredients, which active ingredients are identical to the active ingredients as defined in any one of embodiments 1) to 44) except that one or more atoms have each been replaced by an atom having the same atomic number but an atomic mass different from the atomic mass usually found in nature. Isotopically labelled, especially $^2$H (deuterium) labelled active ingredients and pharmaceutically acceptable salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment only one of the two active ingredients of the pharmaceutical combination is isotopically labelled. In a preferred embodiment of the invention, the active ingredients are not isotopically labelled, or one active ingredient is not isotopically labelled and the other active ingredient is labelled only with one or more deuterium atoms, or both active ingredients are each labelled only with one or more deuterium atoms. In a most preferred embodiment, the active ingredients are not isotopically labelled at all. Isotopically labelled active ingredients may be prepared in analogy to the methods described for the not isotopically labelled active ingredients, but using the appropriate isotopic variation of suitable reagents or starting materials.

The term "about" placed before a numerical value "X" refers in the current application to an interval extending from X minus 10% of X to X plus 10% of X.

Experimental Part

Preparation of COMPOUND 1:

COMPOUND 1 can be prepared according to the procedure as disclosed in WO 2015/186056 or in DOI: 10.1021/acs.jmedchem.7b01236. (Bezencon O. et al., J. Med. Chem. (2017)).

Audiogenic Seizure-Sensitive Juvenile DBA/2J Mouse Model of Generalized Tonic-Clonic Seizures The inbred DBA/2J mouse strain carries an increased general susceptibility for acute generalized convulsive seizures induced by either pharmacological, electrical or, as juvenile, auditory stimuli. At the age of 17 to 28 days (juvenile), they show tonic-clonic convulsions when exposed to a loud tone.

Male juvenile DBA/2J mice (22-24 days old, body weight between 6.6 and 14.5 grams) were used. Each mouse was placed individually in the exposure chamber, an hemispheric acrylic glass dome (diameter: 50 cm) within a sound-attenuated box. After 60 seconds of habituation, an auditory stimulus of mixed frequency tone (15-20 kHz at 110 dB) was played from a speaker placed on the top center of the dome. The stimulus was applied for 60 seconds maximum or until the mouse showed tonic extension of the hind limbs.

The sound-attenuated box was equipped with lights and a camera system in order to observe and record the behavioral seizure response classified as following:

stage 0, no response stage 1, wild running stage 2, clonus
stage 3, tonic extension of the hind limbs.

At the end of the experiment, all mice were euthanized by $CO_2$ inhalation to assess plasma and brain concentrations of drugs and the absence of pharmacokinetic interaction. Briefly, blood was sampled from the vena cava caudalis with a syringe pre-filled with EDTA (ethylenediamine tetraacetic acid) as anticoagulant and centrifuged to yield plasma (for 10 minutes, at 4° C. and 5000 rpm (rounds per minute)). Brain was sampled and homogenized into one volume of cold phosphate buffer (pH 7.4). Following extraction with methanol, concentrations of the compound in plasma and brain were determined using liquid chromatography coupled to mass spectrometry.

Different combination efficacy experiments are performed. Three different first line antiepileptic drugs (i.e. valproic acid (VPA), levetiracetam (LEV) or lamotrigine (LTG)), referred as anti-epileptic drugs (AEDs) below) were used in combination with N-[1-(5-Cyano-pyridin-2-ylmethyl)-1H-pyrazol-3-yl]-2-[4-(1-trifluoromethyl-cyclopropyl)-phenyl]-acetamide (COMPOUND 1). Each experiment consists of four treatment groups:
1. Vehicle (10% Polyethylene glycol400 (PEG400)/90% methylcellulose (0.5% in water; MC0.5%)), 3 h before exposure to the auditory stimulus+vehicle, 1 h before exposure to the auditory stimulus;
2. COMPOUND 1 (in 10% PEG400/90% MC0.5%), 3 h before exposure to the auditory stimulus+vehicle, 1 h before exposure to the auditory stimulus;
3. Vehicle, 3 h before exposure to the auditory stimulus+ AED (in 10% PEG400/90% MC0.5%), 1 h before exposure to the auditory stimulus; and
4. COMPOUND 1 (in 10% PEG400/90% MC0.5%), 3 h before exposure to the auditory stimulus+AED (in 10% PEG400/90% MC0.5%), 1 h before exposure to the auditory stimulus.

The results from the combination efficacy experiments using COMPOUND 1 and valproic acid (VPA) are shown in Table 1.

TABLE 1

Efficacy of COMPOUND 1, VPA or its combination in audiogenic seizure-sensitive juvenile DBA/2J mice, a model of generalized convulsive seizures (n = 9-10/group) with corresponding brain and plasma concentration.

| | | |
|---|---|---|
| Species | Juvenile male audiogenic seizure-sensitive DBA/2J mice (n = 9-10) | |
| Administration | Oral gavage, 5 mL/kg in 10% PEG400/90% MC0.5% | |
| Assessment | Maximal seizure stage observed during exposure to auditory stimulus. Data are show as mean ± Standard Error of the Mean (SEM) | |
| Statistics | Kruskal-Wallis test followed by Dunn's post-hoc analysis:<br>* $p < 0.05$, ** $p < 0.01$, *** $p < 0.001$ vs. vehicle;<br># $p < 0.05$, ## $p < 0.01$, ### $p < 0.01$ vs. COMPOUND 1;<br>+ $p < 0.05$, ++ $p < 0.01$, +++ $p < 0.001$ vs. VPA | |

| | | Treatment group | | | |
|---|---|---|---|---|---|
| | Variable | vehicle + vehicle | COMPOUND 1, 30 mg/kg + vehicle | vehicle + VPA, 30 mg/kg | COMPOUND 1, 30 mg/kg + VPA, 30 mg/kg |
| | Seizure stage | 3.0 ± 0.0 | 1.8 ± 0.2*** | 2.9 ± 0.1## | 2.0 ± 0.3* |
| COMPOUND 1 | Brain concentration total (ng/g) | | 5228 ± 487 | | 5104 ± 375 |
| | Plasma concentration total (ng/mL) | | 3087 ± 297 | | 3148 ± 296 |
| VPA | Brain concentration total (ng/g) | | | 1264 ± 399 | 1006 ± 117 |
| | Plasma concentration total (ng/mL) | | | 23027 ± 3609 | 19933 ± 1648 |

| | | Treatment group | | | |
|---|---|---|---|---|---|
| | Variable | vehicle + vehicle | COMPOUND 1, 30 mg/kg + vehicle | vehicle + VPA, 100 mg/kg | COMPOUND 1, 30 mg/kg + VPA, 100 mg/kg |
| | Seizure stage | 2.9 ± 0.1 | 1.7 ± 0.3 | 2.7 ± 0.2 | 0.1 ± 0.1***; +++ |
| COMPOUND 1 | Brain concentration total (ng/g) | | 5233 ± 343 | | 5984 ± 336 |
| | Plasma concentration total (ng/mL) | | 4621 ± 556 | | 2819 ± 256 |

TABLE 1-continued

Efficacy of COMPOUND 1, VPA or its combination in audiogenic seizure-sensitive juvenile DBA/2J mice, a model of generalized convulsive seizures (n = 9-10/group) with corresponding brain and plasma concentration.

| | | | | |
|---|---|---|---|---|
| VPA | Brain concentration total (ng/g) | | 9278 ± 2535 | 5948 ± 946 |
| | Plasma concentration total (ng/mL) | | 68144 ± 6868 | 63400 ± 3213 |

| | | Treatment group | | | |
|---|---|---|---|---|---|
| | Variable | vehicle + vehicle | COMPOUND 1, 30 mg/kg + vehicle | vehicle + VPA, 200 mg/kg | COMPOUND 1, 30 mg/kg + VPA, 200 mg/kg |
| | Seizure stage | 3.0 ± 0.0 | 1.2 ± 0.2** | 1.7 ± 0.4 | 0.0 ± 0.0***; + |
| COMPOUND 1 | Brain concentration total (ng/g) | | 4387 ± 342 | | 4994 ± 245 |
| | Plasma concentration total (ng/mL) | | 2832 ± 260 | | 2108 ± 118 |
| VPA | Brain concentration total (ng/g) | | | 24746 ± 3564 | 27012 ± 6539 |
| | Plasma concentration total (ng/mL) | | | 108600 ± 9893 | 109520 ± 11385 |

| | | Treatment group | | | |
|---|---|---|---|---|---|
| | Variable | vehicle + vehicle | COMPOUND 1, 10 mg/kg + vehicle | vehicle + VPA, 100 mg/kg | COMPOUND 1, 10 mg/kg + VPA, 100 mg/kg |
| | Seizure stage | 3.0 ± 0.0 | 3.0 ± 0.0 | 2.8 ± 0.2 | 2.1 ± 0.2***; ###; ++ |
| COMPOUND 1 | Brain concentration total (ng/g) | | 1895 ± 75 | | 2043 ± 178 |
| | Plasma concentration total (ng/mL) | | 1128 ± 98 | | 710 ± 80 |
| VPA | Brain concentration total (ng/g) | | | 10124 ± 2040 | 14628 ± 2906 |
| | Plasma concentration total (ng/mL) | | | 53690 ± 4036 | 57270 ± 3762 |

| | | Treatment group | | | |
|---|---|---|---|---|---|
| | Variable | vehicle + vehicle | COMPOUND 1, 10 mg/kg + vehicle | vehicle + VPA, 200 mg/kg | COMPOUND 1, 10 mg/kg + VPA, 200 mg/kg |
| | Seizure stage | 2.9 ± 0.1 | 2.7 ± 0.3 | 1.3 ± 0.3**; # | 0.8 ± 0.3***; ### |
| COMPOUND 1 | Brain concentration total (ng/g) | | 1452 ± 104 | | 1638 ± 52 |
| | Plasma concentration total (ng/mL) | | 2116 ± 175 | | 1155 ± 73 |

TABLE 1-continued

Efficacy of COMPOUND 1, VPA or its combination in audiogenic seizure-sensitive juvenile DBA/2J mice, a model of generalized convulsive seizures (n = 9-10/group) with corresponding brain and plasma concentration.

| | | | |
|---|---|---|---|
| VPA | Brain concentration total (ng/g) | 44222 ± 4088 | 34694 ± 4441 |
| | Plasma concentration total (ng/mL) | 132578 ± 10721 | 122640 ± 11703 |

As can be seen from Table 1, in juvenile DBA/2J mice, combinations of COMPOUND 1 with valproic acid showed a synergistic antiepileptic effect on the induced audiogenic seizure as compared to the effects observed when the drugs were given alone. For instance, the combination of a partially efficacious dose of COMPOUND 1 (30 mg/kg, seizure severity 2, corresponding to clonic seizure) with an inactive dose of valproic acid (100 mg/kg, seizure severity 3, corresponding to the tonic extension of the hind limbs) showed a synergistic antiepileptic effect and led to complete suppression of the audiogenic induced seizures. The synergistic effect is not the result of a pharmacokinetic interaction as plasma and brain concentrations of COMPOUND 1 and valproic acid were similar after administration of the compounds alone or in combination.

The results from the combination efficacy experiments using COMPOUND 1 and levetiracetam (LEV) are shown in Table 2.

TABLE 2

Efficacy of COMPOUND 1, LEV or its combination in audiogenic seizure-sensitive juvenile DBA/2J mice, a model of generalized convulsive seizures (n = 9-10/group) with corresponding brain and plasma concentration.

| | |
|---|---|
| Species | Juvenile male audiogenic seizure-sensitive DBA/2J mice (n = 9-10) |
| Administration | Oral gavage, 5 mL/kg in 10% PEG400/90% MC0.5% |
| Assessment | Maximal seizure stage observed during exposure to auditory stimulus. Data are show as mean ± SEM |
| Statistics | Kruskal-Wallis test followed by Dunn's post-hoc analysis:<br>* $p < 0.05$, ** $p < 0.01$, *** $p < 0.001$ vs. vehicle;<br># $p < 0.05$, ## $p < 0.01$, ### $p < 0.01$ vs. COMPOUND 1;<br>+ $p < 0.05$, ++ $p < 0.01$, +++ $p < 0.001$ vs. LEV |

| | | Treatment group | | | |
|---|---|---|---|---|---|
| | Variable | vehicle + vehicle | COMPOUND 1, 30 mg/kg + vehicle | vehicle + LEV, 3 mg/kg | COMPOUND 1, 30 mg/kg + LEV, 3 mg/kg |
| | Seizure stage | 3.0 ± 0.0 | 1.9 ± 0.2* | 2.6 ± 0.3 | 0.6 ± 0.2***, +++ |
| COMPOUND 1 | Brain concentration total (ng/g) | | 5042 ± 385 | | 5956 ± 330 |
| | Plasma concentration total (ng/mL) | | 4453 ± 283 | | 4534 ± 224 |
| LEV | Brain concentration total (ng/g) | | | 675 ± 82 | 714 ± 59 |
| | Plasma concentration total (ng/mL) | | | 1208 ± 76 | 1230 ± 64 |

| | | Treatment group | | | |
|---|---|---|---|---|---|
| | Variable | vehicle + vehicle | COMPOUND 1, 30 mg/kg + vehicle | vehicle + LEV, 10 mg/kg | COMPOUND 1, 30 mg/kg + LEV, 10 mg/kg |
| | Seizure stage | 3.0 ± 0.0 | 1.6 ± 0.2* | 1.4 ± 0.3* | 0.3 ± 0.2*** |
| COMPOUND 1 | Brain concentration total (ng/g) | | 4370 ± 334 | | 5466 ± 533 |
| | Plasma concentration | | 4460 ± 322 | | 4123 ± 315 |

TABLE 2-continued

Efficacy of COMPOUND 1, LEV or its combination in audiogenic seizure-sensitive juvenile DBA/2J mice, a model of generalized convulsive seizures (n = 9-10/group) with corresponding brain and plasma concentration.

|  |  |  |  |  |  |
|---|---|---|---|---|---|
| LEV | total (ng/mL) Brain concentration total (ng/g) |  |  | 2307 ± 207 | 2149 ± 142 |
|  | Plasma concentration total (ng/mL) |  |  | 4007 ± 199 | 3877 ± 226 |

|  |  | Treatment group | | | |
|---|---|---|---|---|---|
| | Variable | vehicle + vehicle | COMPOUND 1, 30 mg/kg + vehicle | vehicle + LEV, 50 mg/kg | COMPOUND 1, 30 mg/kg + LEV, 50 mg/kg |
| | Seizure stage | 3.0 ± 0.0 | 1.9 ± 0.3 | 0.5 ± 0.2*** | 0.1 ± 0.1***, # |
| COMPOUND 1 | Brain concentration total (ng/g) |  | 4662 ± 275 |  | 4690 ± 399 |
|  | Plasma concentration total (ng/mL) |  | 4142 ± 178 |  | 3715 ± 351 |
| LEV | Brain concentration total (ng/g) |  |  | 11318 ± 1440 | 13484 ± 1379 |
|  | Plasma concentration total (ng/mL) |  |  | 24156 ± 2669 | 26208 ± 2403 |

|  |  | Treatment group | | | |
|---|---|---|---|---|---|
| | Variable | vehicle + vehicle | COMPOUND 1, 10 mg/kg + vehicle | vehicle + LEV, 1 mg/kg | COMPOUND 1, 10 mg/kg + LEV, 1 mg/kg |
| | Seizure stage | 3.0 ± 0.0 | 2.7 ± 0.2 | 3.0 ± 0.0 | 1.6 ± 0.4**, #, ++ |
| COMPOUND 1 | Brain concentration total (ng/g) |  | 1435 ± 55 |  | 1934 ± 100 |
|  | Plasma concentration total (ng/mL) |  | 1318 ± 77 |  | 1498 ± 112 |
| LEV | Brain concentration total (ng/g) |  |  | 224 ± 20 | 310 ± 34 |
|  | Plasma concentration total (ng/mL) |  |  | 541 ± 48 | 564 ± 42 |

|  |  | Treatment group | | | |
|---|---|---|---|---|---|
| | Variable | vehicle + vehicle | COMPOUND 1, 10 mg/kg + vehicle | vehicle + LEV, 3 mg/kg | COMPOUND 1, 10 mg/kg + LEV, 3 mg/kg |
| | Seizure stage | 2.8 ± 0.2 | 2.9 ± 0.1 | 2.1 ± 0.4 | 1.1 ± 0.2**, ## |
| COMPOUND 1 | Brain concentration total (ng/g) |  | 2379 ± 164 |  | 2517 ± 190 |
|  | Plasma concentration total (ng/mL) |  | 1858 ± 116 |  | 1598 ± 111 |
| LEV | Brain concentration |  |  | 677 ± 70 | 787 ± 39 |

TABLE 2-continued

Efficacy of COMPOUND 1, LEV or its combination in audiogenic seizure-sensitive juvenile DBA/2J mice, a model of generalized convulsive seizures (n = 9-10/group) with corresponding brain and plasma concentration.

|  |  |  |  |  |  |
|---|---|---|---|---|---|
|  | total (ng/g) |  |  |  |  |
|  | Plasma concentration total (ng/mL) |  |  | 1170 ± 53 | 1250 ± 53 |

| | | Treatment group | | | |
|---|---|---|---|---|---|
| | Variable | vehicle + vehicle | COMPOUND 1, 10 mg/kg + vehicle | vehicle + LEV, 10 mg/kg | COMPOUND 1, 10 mg/kg + LEV, 10 mg/kg |
| | Seizure stage | 2.3 ± 0.4 | 2.7 ± 0.2 | 1.7 ± 0.4 | 0.6 ± 0.2*, ## |
| COMPOUND 1 | Brain concentration total (ng/g) | | 1965 ± 138 | | 2026 ± 137 |
| | Plasma concentration total (ng/mL) | | 1894 ± 113 | | 1586 ± 142 |
| LEV | Brain concentration total (ng/g) | | | 2131 ± 267 | 2593 ± 169 |
| | Plasma concentration total (ng/mL) | | | 4527 ± 473 | 5779 ± 232 |

| | | Treatment group | | | |
|---|---|---|---|---|---|
| | Variable | vehicle + vehicle | COMPOUND 1, 10 mg/kg + vehicle | vehicle + LEV, 50 mg/kg | COMPOUND 1, 10 mg/kg + LEV, 50 mg/kg |
| | Seizure stage | 3.0 ± 0.0 | 2.7 ± 0.2 | 1.1 ± 0.3**, # | 0.5 ± 0.2***, ### |
| COMPOUND 1 | Brain concentration total (ng/g) | | 1743 ± 158 | | 1811 ± 93 |
| | Plasma concentration total (ng/mL) | | 1785 ± 186 | | 1715 ± 124 |
| LEV | Brain concentration total (ng/g) | | | 11098 ± 886 | 12622 ± 549 |
| | Plasma concentration total (ng/mL) | | | 26502 ± 2814 | 27010 ± 1349 |

As can be seen from Table 2, in juvenile DBA/2J mice, combinations of COMPOUND 1 with levetiracetam showed a synergistic antiepileptic effect on the induced audiogenic seizure as compared to the effects observed when the drugs were given alone. For instance, the combination of an inactive dose of COMPOUND 1 (10 mg/kg, seizure severity 3, corresponding to tonic extension of the hind limbs) and an inactive dose of levetiracetam (1 mg/kg, seizure severity 3, corresponding to the tonic extension of the hind limbs) showed a synergistic antiepileptic effect and led to audiogenic induced seizures of reduced severity (1.6). The synergistic effect is not the result of a pharmacokinetic interaction as plasma and brain concentrations of COMPOUND 1 and LEV were similar after administration of the compounds alone or in combination.

The results from the combination efficacy experiments using COMPOUND 1 and lamotrigine (LTG) are shown in Table 3.

TABLE 3

Efficacy of COMPOUND 1, LTG or its combination in audiogenic seizure-sensitive juvenile DBA/2J mice, a model of generalized convulsive seizures (n = 9-10/group) with corresponding brain and plasma concentration.

| | |
|---|---|
| Species | Juvenile male audiogenic seizure-sensitive DBA/2J mice (n = 9-10) |
| Administration | Oral gavage, 5 mL/kg in 10% PEG400/90% MC0.5% |
| Assessment | Maximal seizure stage observed during exposure to auditory stimulus. Data are show as mean ± SEM |
| Statistics | Kruskal-Wallis test followed by Dunn's post-hoc analysis: <br> * $p < 0.05$, ** $p < 0.01$, *** $p < 0.001$ vs. vehicle; <br> # $p < 0.05$, ## $p < 0.01$, ### $p < 0.01$ vs. COMPOUND 1; <br> + $p < 0.05$, ++ $p < 0.01$, +++ $p < 0.001$ vs. LTG |

| | | Treatment group | | | |
|---|---|---|---|---|---|
| | Variable | vehicle + vehicle | COMPOUND 1, 30 mg/kg + vehicle | vehicle + LTG, 3 mg/kg | COMPOUND 1, 30 mg/kg + LTG, 3 mg/kg |
| | Seizure stage | 2.7 ± 0.2 | 2.0 ± 0.3 | 1.9 ± 0.2 | 0.9 ± 0.3*** |
| COMPOUND 1 | Brain concentration total (ng/g) | | 4558 ± 317 | | 5032 ± 238 |
| | Plasma concentration total (ng/mL) | | 4652 ± 243 | | 4550 ± 293 |
| LTG | Brain concentration total (ng/g) | | | 1491 ± 128 | 1367 ± 100 |
| | Plasma concentration total (ng/mL) | | | 293 ± 27 | 284 ± 18 |

| | | Treatment group | | | |
|---|---|---|---|---|---|
| | Variable | vehicle + vehicle | COMPOUND 1, 30 mg/kg + vehicle | vehicle + LTG, 10 mg/kg | COMPOUND 1, 30 mg/kg + LTG, 10 mg/kg |
| | Seizure stage | 3.0 ± 0.0 | 2.1 ± 0.2 | 1.4 ± 0.3** | 0.2 ± 0.2***, ## |
| COMPOUND 1 | Brain concentration total (ng/g) | | 4224 ± 261 | | 4260 ± 350 |
| | Plasma concentration total (ng/mL) | | 4556 ± 285 | | 3965 ± 372 |
| LTG | Brain concentration total (ng/g) | | | 3262 ± 144 | 3658 ± 310 |

TABLE 3-continued

Efficacy of COMPOUND 1, LTG or its combination in audiogenic seizure-sensitive juvenile DBA/2J mice, a model of generalized convulsive seizures (n = 9-10/group) with corresponding brain and plasma concentration.

|  |  |  |  |  |
|---|---|---|---|---|
|  | Plasma concentration total (ng/mL) |  | 1203 ± 77 | 1332 ± 102 |

| | | Treatment group | | |
|---|---|---|---|---|
| Variable | | vehicle + vehicle | COMPOUND 1, 30 mg/kg + vehicle | vehicle + LTG, 30 mg/kg | COMPOUND 1, 30 mg/kg + LTG, 30 mg/kg |
| | Seizure stage | 3.0 ± 0.0 | 1.9 ± 0.3 | 0.2 ± 0.2***, # | 0.0 ± 0.0***, ## |
| COMPOUND 1 | Brain concentration total (ng/g) | | 3618 ± 159 | | 3286 ± 170 |
| | Plasma concentration total (ng/mL) | | 3968 ± 258 | | 2915 ± 150 |
| LTG | Brain concentration total (ng/g) | | | 8888 ± 248 | 8562 ± 853 |
| | Plasma concentration total (ng/mL) | | | 3562 ± 165 | 2797 ± 475 |

| | | Treatment group | | |
|---|---|---|---|---|
| Variable | | vehicle + vehicle | COMPOUND 1, 10 mg/kg + vehicle | vehicle + LTG, 10 mg/kg | COMPOUND 1, 10 mg/kg + LTG, 10 mg/kg |
| | Seizure stage | 2.9 ± 0.1 | 2.8 ± 0.2 | 1.1 ± 0.3***, ### | 1.4 ± 0.3**, ## |
| COMPOUND 1 | Brain concentration total (ng/g) | | 1197 ± 80 | | 1420 ± 165 |
| | Plasma concentration total (ng/mL) | | 1522 ± 109 | | 1286 ± 140 |
| LTG | Brain concentration total (ng/g) | | | 4054 ± 323 | 3687 ± 393 |
| | Plasma concentration total (ng/mL) | | | 930 ± 77 | 859 ± 101 |

As can be seen from Table 3, in juvenile DBA/2J mice, combinations of COMPOUND 1 with with lamotrigine showed an improved antiepileptic effect on the induced audiogenic seizure as compared to the effects observed when the drugs were given alone. For instance, the combination of a partially efficacious dose of COMPOUND 1 (30 mg/kg, seizure severity 2, corresponding to clonic seizure) and a partially efficacious dose of lamotrigine (3 mg/kg, seizure severity 2, corresponding to clonic seizure) showed an increased antiepileptic effect and led to audiogenic induced seizures of reduced severity (1 corresponding to a wild running). The effect is not the result of a pharmacokinetic interaction as plasma and brain concentrations of COMPOUND 1 and lamotrigine were similar after administration of the compounds alone or in combination.

Pharmaceutical Composition Comprising COMPOUND 1:

A pharmaceutical composition comprising 10 mg of COMPOUND 1 was prepared as hard gelatine capsules (350 mg) using the following ingredients:

| Ingredients | Role | mg/cps | % |
|---|---|---|---|
| COMPOUND 1 | Active Ingredient | 10.00 | 2.86 |
| MCC (Avicel PH101) | Filler 1 | 207.38 | 59.25 |
| Mannitol (Parteck M200) | Filler 2 | 88.87 | 25.39 |
| PVP (Povidone, Kollidon 30) | Binder | 17.50 | 5.00 |
| cross-linked PVP (Crospovidone, Kollidon CL) | Disintegrant | 17.50 | 5.00 |
| Silica anhydrous (Aerosil 200) | Glidant | 5.25 | 1.50 |
| Magnesium Stearate (LUB Stab) | Lubricant | 3.50 | 1.00 |
| Total | | 350.00 | 100.00 |

Abbreviations:
cps: capsule;
MCC: microcrystalline cellulose;
PVP: polyvinylpyrrolidone The hard gelatine capsules can be prepared according to the following process:

| Step | Operation |
|---|---|
| 1 | Sieving of the inner phase (mixture of MCC, Mannitol, Povidone and Crospovidone) with a 800 μm sieve |
| 2 | Blending with a TURBULA ® shaker mixer (10 min at 32 rpm: Mixture A) |
| 3 | Combining of COMPOUND 1 with Mixture A (1:5 by weight) and mixing with a TURBULA ® shaker mixer (15 min at 32 rpm: Mixture B) |
| 4 | Sieving of Mixture B with a 800 μm sieve |
| 5 | Blending of Mixture B with a TURBULA ® shaker mixer (15 min at 32 rpm) |
| 6 | Transferring Mixture B to container with the remaining Mixture A (Mixture C) |
| 7 | Blending of Mixture C with a TURBULA ® shaker mixer (15 min at 32 rpm) |
| 8 | Compacting and granulating on a 800 μm sieve with a roller compactor (Mini-Pactor) |
| 9 | Blending with a TURBULA ® shaker mixer (10 min at 32 rpm) |
| 10 | Sieving of the anhydrous Silica (Glidant) with a 800 μm sieve and adding to Mixture C |
| 11 | Blending with a TURBULA ® shaker mixer (2 min at 32 rpm: Mixture D) |
| 12 | Sieving of the Magnesium Stearate (Lubricant) with a 800 μm sieve and adding to Mixture D |
| 13 | Blending with a TURBULA ® shaker mixer (2 min at 32 rpm: Mixture E) |
| 14 | Encapsulating with hard gelatine capsules Size 0 | rpm: revolutions per minute

The invention claimed is:

1. A pharmaceutical combination comprising a first active ingredient which is N-[1-(5-Cyano-pyridin-2-ylmethyl)-1H-pyrazol-3-yl]-2-[4-(1-trifluoromethyl-cyclopropyl)-phenyl]-acetamide or a pharmaceutically acceptable salt thereof and a second active ingredient selected from the group consisting of (S)-2-(2-oxopyrrolidin-1-yl)butanamide and 2-propylpentanoic acid, or a pharmaceutically acceptable salt of any of the aforementioned.

2. The pharmaceutical combination according to claim 1, wherein the second active ingredient is (S)-2-(2-oxopyrrolidin-1-yl)butanamide or a pharmaceutically acceptable salt thereof.

3. The pharmaceutical combination according to claim 1, wherein the second active ingredient is 2-propylpentanoic acid or a pharmaceutically acceptable salt thereof.

4. The pharmaceutical combination according to claim 1, wherein the first and the second active ingredient are comprised in a single pharmaceutical composition.

5. The pharmaceutical combination according to claim 1, wherein the first and the second active ingredient are comprised in separated pharmaceutical compositions.

6. A method of treating epilepsy in a patient in need thereof, comprising administering to the patient a pharmaceutical combination according to claim 1.

7. A method of treating tonic clonic seizures, absence seizures, or a combination thereof, in a patient in need thereof, comprising administering to the patient a pharmaceutical combination according to claim 1.

8. A kit of parts comprising a first pharmaceutical composition comprising, as an active ingredient, N-[1-(5-Cyano-pyridin-2-ylmethyl)-1H-pyrazol-3-yl]-2-[4-(1-trifluoromethyl-cyclopropyl)-phenyl]-acetamide, or a pharmaceutically acceptable salt thereof, and at least one therapeutically inert excipient; and a second pharmaceutical composition comprising an active ingredient selected from the group consisting of (S)-2-(2-oxopyrrolidin-1-yl)butanamide and 2-propylpentanoic acid, or a pharmaceutically acceptable salt thereof, and at least one therapeutically inert excipient.

* * * * *

UNITED STATES PATENT AND TRADEMARK OFFICE
CERTIFICATE OF CORRECTION

| | | |
|---|---|---|
| PATENT NO. | : 11,213,517 B2 | Page 1 of 1 |
| APPLICATION NO. | : 16/470109 | |
| DATED | : January 4, 2022 | |
| INVENTOR(S) | : Kessler et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 9 days.

Signed and Sealed this
Seventh Day of February, 2023

Katherine Kelly Vidal
*Director of the United States Patent and Trademark Office*